United States Patent [19]

De Clercq et al.

[11] Patent Number: 5,589,615
[45] Date of Patent: *Dec. 31, 1996

[54] PROCESS FOR THE PRODUCTION OF TRANSGENIC PLANTS WITH INCREASED NUTRITIONAL VALUE VIA THE EXPRESSION OF MODIFIED 2S STORAGE ALBUMINS

[75] Inventors: Ann De Clercq, Harelbeke, Belgium; Enno Krebbers, Alhambra, Calif.; Joël Vandekerckhove, Loppem, Belgium; Luiz Barreto De Castro; Eugen Gander, both of Brasileia, Brazil; Marc Van Montagu, Brussels, Belgium

[73] Assignees: Plant Genetic Systems N.V., Ghent, Belgium; Brazilian Agricultural Research Organization-Embrapa/Cenargen, Brasileia, Brazil

[*] Notice: The term of this patent shall not extend beyond the expiration date of Pat. No. 5,487,991.

[21] Appl. No.: 229,069

[22] Filed: Apr. 18, 1994

Related U.S. Application Data

[63] Continuation of Ser. No. 47,538, Apr. 19, 1993, abandoned, which is a continuation of Ser. No. 499,386, Aug. 9, 1990, abandoned.

[30] Foreign Application Priority Data

Oct. 18, 1988 [GB] United Kingdom ................ 88402611
Oct. 20, 1988 [GB] United Kingdom ................ 88402650

[51] Int. Cl.$^6$ .................................................. A01H 4/00
[52] U.S. Cl. ................ 800/205; 800/250; 800/DIG. 15; 800/DIG. 17; 800/DIG. 70
[58] Field of Search ............................... 435/69.1, 172.3, 435/240.4; 530/377, 370; 800/205, 250, DIG. 15, DIG. 17, DIG. 70

[56] References Cited

U.S. PATENT DOCUMENTS

| | | | |
|---|---|---|---|
| 4,885,357 | 12/1989 | Larkins et al. ........................... | 530/373 |
| 5,003,045 | 3/1991 | Hoffman .................................. | 530/378 |
| 5,487,991 | 1/1996 | Vandekerckhove et al. ........ | 435/172.3 |

FOREIGN PATENT DOCUMENTS

| | | |
|---|---|---|
| 0142924 | 7/1985 | European Pat. Off. . |
| 240911A | 11/1986 | German Dem. Rep. ............ 435/172.3 |
| 240911 | 11/1986 | Germany . |
| WO83/01176 | 6/1983 | WIPO . |
| WO87/00865 | 4/1987 | WIPO . |
| WO87/07299 | 9/1987 | WIPO . |
| WO89/03387 | 5/1989 | WIPO . |

OTHER PUBLICATIONS

Expression of the 2S albumin from *Bertholletia excelsa* in *Brassica napus*, Guerche et al., Mol Gen Genet (1990) 221:306–314.

Expression and Processing of an *Arabidopsis* 2S albumin in Transgenic Tobacco, De Clercq et al., Plant Physiol. (1990) 899–907.
Altenbach et al, *J. of Cell. Biochem., Suppl.* 12 C, p. 177, abstract L 300 (1988).
Altenbach et al, *J. of Cell. Biochem., Suppl.* 11B, p. 46, abstract F401 (1987).
Altenbach et al, *Plant Mol. Biol.*, vol. 8, No. 3, pp. 239–250 (1987).
Ampe et al, *Eur. J. Biochem.*, vol. 159, pp. 597–604 (1986).
Dickinson et al, *Proc. Natl. Acad. Sci. USA*, vol. 84, pp. 5525–5529 (1987).
Donaldson et al, *J. of Cell. Biochem.*, vol. 0, No. 10, part D, p. 53, abstract N137 (1986).
Knauf, Proceedings, World Conf. Energing Technology, Fat Oils, pp. 340–342 (1985).
Krebbers et al, *Biological Abstracts*, vol. 86, No. 12, pp. 471–472, 124569 (1988).
Lawton et al, *Plant Molecular Biology*, vol. 9, pp. 315–324 (1987).
Radke et al, *Theor. Appl. Genet.*, vol. 75, pp. 685–694 (1988).
Saalbach et al, *Chemical Abstracts*, vol. 108, p. 193, 162663u (1988).
Scofield et al, *J. of Biol. Chem.*, vol. 262, No. 25, pp. 12202–12208 (1987).
Slightom et al, *Biotech. Adv.*, vol. 5, pp. 29–45 (1987).
Vandekerckhove et al, *Bio/Technology*, vol. 7, pp. 929–932 (Sep. 1989) [not prior art].
Vincent, *Biofutur*, pp. 48–52 (Sep. 1988) [not prior art].
Schwenke et al, *Biochem. Physiol. Pflanzen*, vol. 183, pp. 219–224 (1988).
Zell et al., EMBO Journal, vol. 6, No. 6 pp. 1809–1815, 1987.
De Clercq et al., Plant Physiol. (1990) 94, pp. 970–979.
Gould et al., Plant Physiol. (1991) 95, pp. 426–434.
Hoffman et al., Plant Molecular Biology 11: pp. 717–729 1988.
Saalbach et al., "Expression of Modified Legumes Storage . . . " pp. 151–158 in Genetic Engineering of crop plants (1990) Proc. 49th Nottingham Easter School, Butterworth, London.
Sayler et al (1990) Plant Molecular Bioloy 15 879.
Kortt, et al (1991) Eur. J. Biochem 195:329–334.
Dickinson, et al (1987) Fed. Proc. Fed. Am. Soc. Exp. Biol. 46(6):2023.
Potrykus (Jun. 1990) Bio/Technology 8: 535–542.
Ericson et al (Nov. 1986) The Journal of Biological Chemistry 261 (31): 14576–14581.

*Primary Examiner*—Che S. Chereskin
*Attorney, Agent, or Firm*—Keck, Mahin & Cate

[57] ABSTRACT

A process for the production of plants with increased content of appropriate amino acids having high nutritional properties through the modification of plant genes encoding plant storage proteins, particularly the 2S albumins. Seed-forming plants susceptible to Agrobacterium transformation, the genome of which plants includes a recombinant DNA encoding a precursor of a modified 2S albumin, under the control of a promoter, are described, including the particular recombinant DNA.

19 Claims, 21 Drawing Sheets

FIG. 1

| | SIGNAL PEPTIDE | A.T.P.F. | SMALL SUBUNIT | I.P.F. | LARGE SUBUNIT | C.T.P.F. |
|---|---|---|---|---|---|---|
| ARABIDOPSIS | 21 | 16 | 36 | 10 | 79 | 2 |
| BRASSICA | 21 | 16 | 29, 35 | 19 | 86 | 1 |
| BERTHOLLETIA | 22 | 14 | 34 | 5 | 73 | 4 |

FIG. 2A

SIGNAL PEPTIDE

| | | | | | | | | | | | | | | | | | | | | | | |
|---|---|---|---|---|---|---|---|---|---|---|---|---|---|---|---|---|---|---|---|---|---|---|
| B. EXCE. | M | A | K | I | S | V | A | A | A | L | V | L | M | A | L | G | H | A | T | A | | (22) |
| B. NAPUS | M | A | N | K | L | F | L | V | S | A | T | L | – | F | L | L | T | N | A | | | (21) |
| AT2S1 | M | A | N | K | L | F | L | V | C | A | A | L | – | C | F | L | L | T | N | A | | (21) |
| AT2S2 | M | A | N | K | L | F | L | V | C | A | T | L | – | C | F | L | L | T | N | A | | (++) |
| AT2S3 | M | A | N | K | L | F | L | V | C | A | T | L | – | C | F | L | L | T | N | A | | (++) |
| AT2S4 | M | A | N | K | L | F | L | V | C | A | A | L | – | C | F | I | L | T | N | A | | (++) |

AMINO TERMINAL PROCESSED FRAGMENT

| | | | | | | | | | | | | | | | | |
|---|---|---|---|---|---|---|---|---|---|---|---|---|---|---|---|---|
| B. EXCE. | – | F | R | A | T | V | T | T | T | V | V | – | E | E | E | N | (14) |
| B. NAPUS | S | I | Y | R | T | V | V | E | F | D | E | D | D | A | T | N | (16) |
| AT2S1 | S | I | Y | R | T | V | V | E | F | E | E | D | D | A | T | N | (16) |
| AT2S2 | S | I | Y | R | T | V | V | E | F | D | E | D | D | A | S | N | (++) |
| AT2S3 | S | I | Y | R | T | V | V | E | F | E | E | D | D | A | S | N | (++) |
| AT2S4 | S | V | Y | R | T | V | V | E | F | D | E | D | D | A | S | N | (++) |

INTERNAL PROCESSED FRAGMENT

|           | P | Y | Q | T | M |   |   |   |   |   |   |     |
|-----------|---|---|---|---|---|---|---|---|---|---|---|-----|
| B. EXCEL. | G | P | N | W | T | L | D | G | E | F | D | F E D D M E N |
| B. NAPUS  | – | – | – | – | – | – | – | – | E | F | D | F E D D M E N    ( 5) |
| AT2S1     | – | G | P | – | – | – | – | – | E | F | D | F E D D M E N   (19) |
| AT2S2     | – | G | P | – | – | S | L | D | D | E | F | D L E D D M E N   (10) |
| AT2S3     | – | G | P | – | – | S | L | D | D | E | F | D – E D D I E N   (++) |
| AT2S4     | – | – | – | – | – | S | L | D | D | E | F | D M E D D I E N   (++) |

LARGE SUBUNIT

|           |   |   |   |   |   |   |   |   |   |   |   |   |   |   |   |   |   |   |   |
|-----------|---|---|---|---|---|---|---|---|---|---|---|---|---|---|---|---|---|---|---|
| R. COMM.  | P | R | R | G | M | E | Q | E | R | – | S | L | R | G | C | C | D | H | L K Q M Q – S Q – |
| B. EXCEL. | P | Q | G | M | E | P | H | M | S | E | – | – | Q | C | C | C | E | Q L E G M D – E S |
| B. NAPUS  | P | Q | G | P | Q | R | P | L | L | Q | Q | C | C | N | E | L H Q – – E E P |
| AT2S1     | P | Q | G | P | Q | E | Q L | F | L | Q | Q | C | C | N | E | L R Q – – E E P |
| AT2S2     | P | Q | G | P | Q | G | H | I | L | Q | Q | C | C | S | E | L R Q – – E E P |
| AT2S3     | F | E | G | P | Q | G | Y | L | L | Q | Q | C | C | N | E | L R Q – – E E P |
| AT2S4     | P | – | – | – | Q | R | R | Q | L | L | Q | K | C | C | S | E | L R Q – – E E P |

FIG. 2D

| | | | | | | | | | | | | | | | | | | | | | | | |
|---|---|---|---|---|---|---|---|---|---|---|---|---|---|---|---|---|---|---|---|---|---|---|---|
| R. COMM. | - | C | R | C | E | G | L | R | Q | A | - | - | - | - | - | I | Q | Q | - | Q | - | Q | Q |
| B. EXCEL. | - | C | R | C | E | G | L | R | M | M | M | R | M | Q | E | E | M | - | Q | Q | L | - | Q |
| B. NAPUS | L | C | V | C | P | T | L | K | G | A | S | K | A | V | K | Q | Q | I | Q | G | Q | Q | P |
| AT2S1 | D | C | V | C | P | T | L | K | Q | A | A | K | A | V | R | L | Q | G | Q | - | H | Q | P |
| AT2S2 | V | C | V | C | P | T | L | R | Q | A | A | R | A | V | S | L | Q | G | Q | - | H | G | P |
| AT2S3 | V | C | V | C | P | T | L | R | Q | A | A | R | A | V | S | L | Q | G | Q | - | H | G | P |
| AT2S4 | V | C | V | C | P | T | L | R | Q | A | A | K | A | V | R | F | Q | G | Q | Q | H | Q | P |

| | | | | | | | | | | | | | | | | | | | | | | | |
|---|---|---|---|---|---|---|---|---|---|---|---|---|---|---|---|---|---|---|---|---|---|---|---|
| | | | | | | | | | | | | | | | | Q | | | | | | | |
| | | | | | | | | | | | | | | | | M | P | F | | | | | |
| | | | | | | | | | | | | | | | | P | R | Q | P | F | | | |
| | | | | | | | | | | | | | | | | Q | Q | Q | P | E | | | |

| | | | | | | | | | | | | | | | | | | | | | | | |
|---|---|---|---|---|---|---|---|---|---|---|---|---|---|---|---|---|---|---|---|---|---|---|---|
| R. COMM. | G | - | Q | N | V | F | E | A | F | R | T | A | A | N | L | P | S | M | C | G | V | S | P | T |
| B. EXCEL. | G | E | - | Q | M | - | R | M | M | R | L | A | E | N | - | P | S | R | C | N | L | S | P | M |
| B. NAPUS | G | K | Q | Q | M | V | S | R | I | Y | Q | T | A | T | H | L | P | K | V | C | N | I | - | P |
| AT2S1 | - | - | - | - | V | R | K | I | Y | Q | T | A | K | H | L | P | N | V | C | D | I | - | P |
| AT2S2 | - | - | - | - | S | R | K | I | Y | K | T | A | K | Y | L | P | N | I | C | K | I | - | Q |
| AT2S3 | - | - | - | - | S | R | K | I | Y | Q | T | S | A | K | Y | L | P | N | I | C | K | I | - | Q |
| AT2S4 | - | - | - | - | V | R | K | I | Y | Q | T | A | A | K | Y | L | P | N | I | C | K | I | - | Q |

FIG. 2E

| | | | | | | | | | | | | |
|---|---|---|---|---|---|---|---|---|---|---|---|---|
| R. COMM. | Q | – | – | C | R | F | | | | | | |
| B. EXCEL. | R | – | – | C | P | M | G | G | S | | | |
| B. NAPUS | V | S | V | C | P | F | Q | K | T | M | P | G | – | P | S |
| AT2S1 | V | D | V | C | P | F | N | – | I | P | S | F | P | S | (61) |
| AT2S2 | V | G | E | C | P | F | Q | T | T | I | P | F | F | P | P | (73) |
| AT2S3 | V | G | E | C | P | F | Q | T | T | I | P | F | F | P | P | (86) |
| AT2S4 | V | G | V | C | P | F | Q | – | – | I | P | S | I | P | S | (79) |
| | | | | | | | | | | | | | | | (++) |
| | | | | | | | | | | | | | | | (++) |
| | | | | | | | | | | | | | | | (++) |

CARBOXYL TERMINAL PROCESSED FRAGMENT

| | | | | | |
|---|---|---|---|---|---|
| B. EXCEL. | I | A | G | F | |
| B. NAPUS | Y | – | | | ( 4) |
| AT2S1 | F | Y | | | ( 1) |
| AT2S2 | Y | – | | | ( 2) |
| AT2S3 | Y | Y | | | (++) |
| AT2S4 | Y | Y | | | (++) |
| | | | | | (++) |

FIG. 4A

```
                                                  ATCTTTATCCA  -421
TATATTGTCTTACCATCAATAGACAATATCCAATGGACCGGTTGACCTGCCTGTATAAGTA  -361
ATTTTTCAAGATGCTAAAACTTTTTATGTATTTCAGAATTAACCTCCAAAAACATTTATTG  -301
ACACTACTACTCTTTCCGTATTGACTCTCAACTAGTCATTTCAAAATAATTGACATGT    -241
CAGAACATGAGTTACACATGGTTGCATATTGCAAGTAGACAACAATCATATAGCTCTGCT  -181
TTACATTTGAGTTCCAACACCTAATCACGACAAACTCATCATATAGTCTCTCTTTTCTCACTTCCT  -121
AAACATATGCATGTATTCTTACACGTGAACTCCATGCAAGTCTCTTTCTCACCTATAAA   -61
TACCAACCACACCTTCACCACATTCTTCACTGAACCAAAAACATACACACATAGCAAAAA  -1

M  A  N  K  L  F  L  V  C  A  A  L  A  L  C  F  L  L  T  N    20
           ATGGCAAAACAAGTGTTCCTCGTCTGGCAGCTCTCGCTCTGCTTCCTCCTCCTCACCAAC  60
                                                       *Start SSU
            A *S  I  Y  R  T  V  V  E  F  E  E  E  D  D  A  T  N *P  I  G    40
           GCTTCCATCTACCGCACCGTCGTTGAGTTCGAAGAAGATGACGCCACTAACCCCATAGGC  120
```

FIG. 4B

```
  P  K  M  R  K  C  R  K  E  F  Q  K  E  Q  H  L  R  A  C  Q        60
CCAAAAATGAGGAAATGCCGCAAGGAGTTTCAGAAAGAACACCTAAGAGCTTGCCAG          180
                            *Processed -->
  Q  L  M  L  Q  Q  A  R  Q  G  R  S  D *E  F  D  F  E  D  D        80
CAATTGATGCTCCAGCAAGCAAGGCAAGGCCGTAGCGATGAGTTTGATTTCGAAGACGAC      240
               * Large subunit -->
  M  E  N *P  Q  G  Q  Q  Q  E  Q  Q  L  F  Q  Q  C  C  N  E       100
ATGGAGAACCCACAGGGACAACAACAGGAACAACAGCTATTCCAGCAGTGCTGCAACGAG      300

L  R  Q  E  E  P  D  C  V  C  P  T  L  K  Q  A  A  A  K  A  V    120
CTTCGCCAGGAAGAGCCAGATTGTGTTTGCCCCACCTTGAAACAAGCTGCCAAGGCCGTT      360
         oligonucleotide 5'-CAAGCTGCCAAGTACCGT
                               K  Y  G
```

FIG. 4C

```
           R L Q G Q H Q P M Q V R K I Y Q T A K H    140
AGACTCCAGGGACAGCACCAACCAATGCAAGTCAGGAAAATTTACCAGACAGCCAAGCAC    420
                              GGATTCTTGAAGCAGCACCAAC-3' oligo
                               G F L K
           L P N V C D I P Q V D V C P F N I P S F    160
TTGCCCAACGTTTGCGACATCCCGCAAGTTGATGTTTGTCCCTTCAACATCCCTTCATTC    480
*End mat. 1g. su.
 P  S* F Y *                                                    164
CCTTCTTTCTACTAAATCTCAAACAAAAACCCTCAAAGGTATGAGAGTGTGGTTGTTGATA    540

TATACATGTTGACACTTGACACATACCACACTCATCGTCGTGTTTTATGATAAATGT       597
```

FIG. 5

```
GGICAICAICAIGAICAICAITTITTICAICAITGITGITGIAAIGA
 P  Q  Q  Q  Q  E  Q  Q  L  F  Q  Q  C  N  E  L  R  Q  E  E  P  D  C  V  C  P  T  L
                                                                            CCIAAI
AAICAIGCIGCIAAIGCIGTIIGITTICAIGGICAICAICA
 K  Q  A  A  K  A  V  R  L  Q  G  Q  H  Q  P  M  Q  V  R  K  I  Y  Q  T  A  K  H  L  P  N

GTTTGIGAIATTCCICAIGTIGAIGTTTGICCITTIAAICC
 V  C  D  I  P  Q  V  D  V  C  P  F  N  P
```

| | | | | | | | | | | | | |
|---|---|---|---|---|---|---|---|---|---|---|---|---|
| R. comm. | P | R | R | G | M | E | P | Q | E | R | – | S | L | R | G | | D | H | L | K | Q | M | Q | – | S | Q |
| B. excel. | P | Q | G | P | Q | Q | Q | M | E | P | H | M | S | E | – | 3 4 | C | E | Q | L | E | G | M | D | E | – |
| B. napus | P | Q | G | P | Q | Q | Q | Q | E | Q | R | P | P | L | Q | | C | N | E | L | H | Q | – | E | E | P |
| AT2S1 | P | Q | G | P | Q | Q | Q | Q | G | H | Q | Q | L | H | L | | C | Q | E | L | R | Q | – | E | E | P |
| AT2S2 | P | Q | G | P | Q | Q | Q | Q | G | Y | R | Q | L | L | L | | C | Q | E | L | R | Q | – | E | E | P |
| AT2S3 | F | E | G | P | Q | Q | – | – | R | R | Q | L | L | L | | C | N | E | L | R | Q | – | E | E | P |
| AT2S4 | P | – | – | – | – | – | Q | R | R | Q | L | L | Q | K | | C | S | E | L | R | Q | – | E | E | P |

| | | | | | | | | | | | | | |
|---|---|---|---|---|---|---|---|---|---|---|---|---|---|
| R. comm. | – | – | – | – | – | – | – | – | – | – | I | Q | Q | Q | – | I | Q | Q | Q | – | L | Q | – | Q |
| B. excel. | – | – | – | – | – | – | – | – | – | – | E | E | M | – | Q | Q | P | R | – | Q | Q | Q | – | Q |
| B. napus | – | – | – | – | L | R | Q | A | – | R | M | Q | Q | E | – | I | Q | Q | Q | H | G | – | P | M | Q |
| AT2S1 | 5 | 6 | C | R | C | E | G | L | R | Q | A | M | R | M | Q | Q | I | L | Q | G | Q | H | – | P | M | Q |
| AT2S2 | – | – | C | R | C | E | G | L | R | M | M | M | R | Q | K | A | V | R | L | Q | G | Q | H | G | – | P | F | Q |
| AT2S3 | L | C | V | C | P | T | L | K | G | A | S | K | A | V | K | Q | A | V | S | L | Q | G | Q | H | G | – | P | F | Q |
| AT2S4 | V | C | V | C | P | T | L | K | Q | A | A | R | A | V | S | Q | A | V | R | F | Q | G | Q | H | Q | P | E | Q |

FIG. 6B(2)

```
              ↓7                              
R. comm.  G--QNVFEAFRTAANLPSMCGVSPT
B. excel. GE-QM-RRMRLAENIPSRCNLPMQ
B. napus  GKQQMVSRIQTATHLPKVCNI-PQ
AT2S1     ------VRKIYQTAKHLPNVCDI-PQ
AT2S2     ------SRKIYKTAKYLPNICKI-QQ
AT2S3     ------SRKIYQSAKYLPNICKI-QQ
AT2S4     ------VRKIYQAAKYLPNICKI-QQ ↓8
R. comm.  Q--CRF
B. excel. R--CPMGGS
B. napus  VSVCPFQKTMPG-PS
AT2S1     VDVCPFN-IPSFPS
AT2S2     VGECPFTTIPFFPP
AT2S3     VGECPFTTIPFFPP
AT2S4     VGVCPFQ--IPSIPS
```

```
GT'  AT  AC
CA   TA' TG          AccI site
```

```
AAA GGT ATA ATG ATG ATG ATG ATG ATG CGC ATG ATA CAC               Example I
TTT CCA TAT TAC TAC TAC TAC TAC GCG TAC TAT GTG
```

```
AAA CGT ATA ATG ATG ATG ATG CAA CCA AGG GGC GAT ATG ATA ATG ATA ATG ATG A
TTT GCA TAT TAC TAC TAC TAC GTT GGT TGG CCG GTA TAC TAC TAT TAC TAC TAC T
```

```
CAA CCA AGG GGC GAT ATG ATG ATG ATA CAC      Example II
GTT GGT TCC GCG CTA TAC TAC TAC TAT GTG
```

FIG. 7

AT2S1 = unmodified large subunit of AT2S1
Del HV = deletion of the AT2S1 HV region
Subst 1 = substitution by IMMMRM
Subst 2 = substitution by
IMMMQPRGDMMMIMMMQPRGDMMM

|       | Sequence | Number of methionines in the large subunit |
|-------|----------|---|
| AT2S1   | P Q G Q Q Q E Q Q L F Q Q C C N E L R Q — — E E P D C V C P T L K — I | 1 |
| Del HV  | P Q G Q Q Q E Q Q L F Q Q C C N E L R Q — — E E P D C V C P T L K G I | 0 |
| Subst 1 | P Q G Q Q Q E Q Q L F Q Q C C N E L R Q — — E E P D C V C P T L K G I | 5 |
| Subst 2 | P Q G Q Q Q E Q Q L F Q Q C C N E L R Q — — E E P D C V C P T L K G I | 12 |

|       | Sequence |
|-------|----------|
| AT2S1   | Q A A K A V R L Q G Q H Q P M Q — V R K I Y Q T A K — H L P N V C D I |
| Del HV  | — — — — — — — — — — — — — — — — — — — — — — — — — I H L P N V C D I |
| Subst 1 | M M M R M — — — — — — — — — — — — — — — — — — — — I H L P N V C D I |
| Subst 2 | M M M Q P R G D M M M I M M M Q P R G D M M M — — — I H L P N V C D I |

|       | Sequence |
|-------|----------|
| AT2S1   | — P Q V D V C P F N — — I P S F P S |
| Del HV  | — P Q V D V C P F N — — I P S F P S |
| Subst 1 | — P Q V D V C P F N — — I P S F P S |
| Subst 2 | — P Q V D V C P F N — — I P S F P S |

PROCESS FOR THE PRODUCTION OF TRANSGENIC PLANTS WITH INCREASED NUTRITIONAL VALUE VIA THE EXPRESSION OF MODIFIED 2S STORAGE ALBUMINS

This is a continuation of application of Ser. No. 08/047,538 filed on Apr. 19, 1993 now abandoned, which was a continuation of Ser. No. 07/499,386, filed Aug. 9, 1990, now abandoned.

This invention relates to a process for the production of plants with increased content of appropriate amino acids having high nutritional properties through the modification of plant genes encoding plant storage proteins, more particularly the 2S albumins.

More particularly, the invention aims at providing genetically modified plant DNA and plant live material including said genetically modified DNA replicable with the cells of said plant material, which genetically modified plant DNA contains sequences encoding a polypeptide containing said appropriate amino acids,the expression of which is under the control of a suitable plant promoter.

A further object of the invention is to take advantage of the capacity of 2S albumins to be produced in large amounts in plants.

A further object of the invention is to take advantage of a hypervariable region of the 2S albumins, the supplementing of which with a number of said appropriate amino acid codons in said hypervariable region of the gene encoding said 2S albumins, does not disturb the correct expression, processing and transport of produced modified storage proteins in the protein bodies of the plants.

Animals and men obtain directly or indirectly their essential amino acids by eating plants. These essential amino acids include lysine, tryptophan, threonine, methionine, phenylalanine, leucine, valine and isoleucine. For ease of description these amino acids are called "appropriate amino acids". Rather recently, agricultural scientists concerned with the world±hunger problem, concentrated their work on developing plants with high nutritional yield. These new varieties, obtained through breeding in most cases, were richer in carbohydrates but usually poorer in essential proteins than the wild type varieties from which they were derived. Currently, increasing recognition of the role of plants in supplying essential amino acids to the animal world had led to an emphasis on the development of new food plants having a better amino acid content. Classical breeding however has limitations for achieving this goal. Molecular genetics, on the contrary, offers a possibility to overcome these difficulties. Reference is made to the European patent application 80208418 and the communication of Brown et al., 1986, in which a gene encoding a corn seed storage protein, (the so called zeins) is modified by the addition of sequences encoding lysine codons.

Seed storage proteins represent up to 90% of total seed protein in seeds of many plants. They are used as a source of nutrition for young seedlings in the period immediately after germination. The genes encoding them are strictly regulated, being expressed in a highly tissue specific and stage specific fashion (Walling et al., 1986; Higgins, 1984). Thus they are expressed almost exclusively in developing seed, and different classes of seed storage proteins may be expressed at different stages in the development of the seed. They are generally restricted in their intercellular location, being stored in membrane bound organelles called protein bodies or protein storage vacuoles. These organelles provide a protease-free environment, and often also contain protease inhibitors. A related group of proteins, the vegetative storage proteins, have similar amino acid compositions and are also stored in specialized vacuoles, but are found in leaves instead of in seeds (Staswick, 1988). These proteins are degraded upon flowering, and are thought to serve as a nutritive source for developing seeds.

The expression of foreign genes in plants is well established (De Blaere et al., 1987). In several cases seed storage protein genes have been transferred to other plants. In most of these cases it was shown that within its new environment the transferred seed storage protein gene is expressed in a tissue specific and developmentally regulated manner (Beachy et al., 1985; Sengupta-Gopalan et al., 1985; Marris et al., 1988; Ellis et al., 1988; Higgins et al., 1986, Okamuro et al., 1986). It has also been shown in at least two cases that foreign seed storage proteins are located in the protein bodies of the host plant (Greenwood and Chrispeels, 1985; Hoffman et al., 1987). It has further been shown that stable and functional messenger RNA's can be obtained if a cDNA, rather than a complete gene including introns, is used as the basis for the chimeric gene (Chee et al., 1986).

Storage proteins are generally classified on the basis of solubility and size (more specifically sedimentation rate, for instance as defined by Svedberg (in Stryer, L., Biochemistry, 2nd ed., W. H. Freeman, New York, page 599)). A particular class of seed storage proteins has been studied, the 2S seed storage proteins, which are water soluble albumins. They represent a significant proportion of the seed storage proteins in many plants (Youle and Huang, 1981) (Table I) and their small size and consequently simpler structure makes them an attractive target for modification (see also patent application EP 87 402 348.4). Several 2S storage proteins have been characterized at either the protein, cDNA or genomic clone levels (Crouch et al., 1983; Sharief and Li, 1982 Ampe et al., 1986; Altenbach et al., 1987; Ericson et al., 1986; De Castro et al., 1987; Scofield and Crouch, 1987; Josefsson et al., 1987; EP 87.4023484, Krebbers et al., 1988). 2S albumins are formed in the cell from two subunits of 6–9 and 3–4 kilodaltons (kd) respectively, which are linked by disulfide bridges.

The work in the references above showed that 2S albumins are synthesized as complex prepropeptides whose organization is shared between the 2S albumins of many different species and are shown diagrammatically for three of these species in FIG. 1. Several complete sequences are shown in FIG. 2.

As to FIG. 2 relative to protein sequences of 2S albumins, the following observations are made. For *B. napus, B. excelsia* , and *A. thaliana* both the protein and DNA sequences have been determined, for *R. communis* only the protein sequence is available (*B. napus* from Crouch et al., 1983 and Ericson et al., 1986; *B. excelsia* from Ampe et al., 1986, De Castro et al., 1987 and Altenbach et al., 1987, *R. communis* from Sharief and Li, 1982). Boxes indicate homologies, and raised dots the position of the cysteines.

Comparison of the protein sequences at the beginning of the precursor with standard consensus sequences for signal peptides reveals that the precursor has not one but two segments at the amino terminus which are not present in the mature protein, the first of which is a signal sequence (Perlman and Halvorson, 1983) and the second of which has been designated as the amino terminal processed fragment (the so-called ATPF). Signal sequences serve to ensure the co-translational transport of the nascent polypeptide across the membrane of the endoplasmic reticulum (Blobel, 1980), and are found in many types of proteins, including all seed storage proteins examined to date (Herman et al., 1986).

This is crucial for the appropriate compartmentalization of the protein. The protein is further folded in such a way that correct disulfide bridges are formed. This process is probably localized at the luminal site of the endoplasmatic reticulum membrane, where the enzyme disulfide isomerase is localized (Roden et al., 1982; Bergman and Kuehl, 1979). After translocation across the endoplasmic reticulum membrane it is thought that most storage proteins are transported via said endoplasmic reticulum to the Golgi bodies, and from the latter in small membrane bound vesicles ("dense vesicles") to the protein bodies (Chrispeels, 1983; Craig and Goodchild, 1984; Lord,1985). That the signal peptide is removed co-translationally implies that the signals directing the further transport of seed storage proteins to the protein bodies must reside in the remainder of the protein sequence present. Zeins and perhaps some other prolaminins deviate from this pathway; indeed the protein bodies are formed by budding directly off of the endoplasmic reticulum (Larkins and Hurkman, 1978). As already of record, 2S albumins contain sequences at the amino end of the precursor other than the signal sequence which are not present in the mature polypeptide. This is not general to all storage proteins. This amino terminal processed fragment is labeled ATPF in FIG. 1.

In addition, as shown in FIG. 1, several amino acids located between the small and large subunits in the precursor are removed (labeled IPF in the figure, which stands for internal processed fragment). Furthermore, several residues are removed from the carboxyl end of the precursor (labeled CTPF in the figure which stands for carboxyl terminal processed fragment). The cellular location of these latter processing steps is uncertain, but is most likely the protein bodies (Chrispeels et al., 1983; Lord, 1985). As a result of these processing steps the small subunit and the large subunit remain. These are linked by disulfide bridges, as discussed below.

When the protein sequences of 2S albumins of different plants are compared strong structural similarities are observed. This is more particularly illustrated by FIG. 2 which provides the amino acid sequences of the small subunit and large subunit respectively of representative 2S storage seed albumin proteins of different plants, i.e.,:
R. comm. : Ricinus communis
A. thali.: Arabidopsis thaliana
B. napus: Brassica napus
B. excel.: Bertholletia excelsia (Brazil nut)
It must be noted that in FIG. 2:
the amino acid sequences of said subunits extend on several lines; the cysteine groups of the amino acid sequences of the exemplified storage proteins and identical amino acids in several of said proteins have been brought into vertical alignment; the hyphen signs which appear in some of these sequences represent absent amino acids, in other words direct linkages between the closest amino acids which surrounded them;
the amino acid sequences which in the different proteins are conserved are framed.

It will be observed that all the sequences contain eight cysteine residues (the first and second in the small subunit, the remainder in the large subunit) which could participate in disulfide bridges as diagrammatically shown in FIG. 3, which represents a hypothetical model (for the purpose of the present discussion) rather than a representation of the true structure of the 2S albumin of *Arabidopsis thaliana*.

Said hypothetical model has been inspired by the disulfide bridge mediated loop-formation of animal albumins, such as serum albumins (Brown, 1976), alpha-fetoprotein (Jagodzinski et al., 1987; Morinaga et al., 1983) and the vitamine D binding protein where analogous constant C—C doublets and C-X-C triplets, were observed (Yang et al., 1985). As can be seen in FIG. 2, the regions which are intercalated between the first and second cysteines, between the fifth and sixth cysteines, and between the seventh and eight cysteines of the mature protein show a substantial degree of conservation or similarity. It would thus seem that these regions are in some way essential for the proper folding and/or stability of the protein when synthesized in the plants. An exception to this conservation exists in the distance between the sixth and seventh cysteine residues. This suggests that these arrangements are structurally important, but that some variation is permissible in the large subunit between said sixth and seventh cysteines where little conservation of amino acids is observed. An analogous suggestion has been made by Slightom and Chee (1987), where the viciline type seed storage proteins from peas were compared. These authors indeed suggest that amino acid replacement mutations designed to increase the number of sulphur containing amino acids should be placed in regions which show little or no conservation of amino acid sequences. The authors however conclude that the proof that such modifications can be tolerated will need to be tested in the seeds of transgenic plants. Moreover, the teaching provided in their paper on the properties of the deletion modified storage protein concerns only the influence on expression levels and not on processing of said storage proteins.

An embodiment of this invention is the demonstration that a well chosen region of the 2S albumin allows variation without altering the properties and correct processing of said modified storage protein in plant cells of transgenic plants.

This region (diagrammatically shown in FIG. 3 by an enlarged hatched portion) will in the examples hereafter referred to be termed as the "hypervariable region". FIG. 3 also shows the respective positions of the other parts of the precursor sequence, including the "IPF" section separating the small subunit and large subunit of the precursor, as well as the number of amino acids (aa) in substantially conserved portions of the protein subunits cysteine residues. The processing cleavage sites (as determined by Krebbers et al., 1988) are shown by symbols.

The seeds of many plants contain albumins of approximately the same size as the storage proteins discussed above. However, for ease of description, this document will use the term "2S albumins" to refer to seed proteins whose genes encode a peptide precursor with the general organization shown in FIG. 1 and which are processed to a final form consisting of two subunits linked by disulfide bridges. The process of the invention for producing plants with an increased content of appropriate amino acids comprises:

- cultivating plants obtained from regenerated plant cells or from seeds of plants obtained from said regenerated plant cells over one or several generations, wherein the genetic patrimony or information of said plant cells, replicable within said plants, includes a nucleic acid sequence, placed under the control of a plant promoter, which can be transcribed into the mRNA encoding at least part of the precursor of a 2S albumin including the signal peptide of said plant, said nucleic acid being hereafter referred to as the "precursor encoding nucleic acid"
- wherein said nucleic acid contains a nucleotide sequence (hereafter termed the "relevant sequence") which relevant sequence comprises a nonessential region modified by a heterologous nucleic acid insert forming an open reading frame in reading phase with the non modified parts surrounding said insert in said relevant sequence.

wherein said insert includes a nucleotide segment encoding a polypeptide containing appropriate amino acids.

It will be appreciated that under the above mentioned conditions each and every cell of the cultivated plant will include the modified nucleic acid. Yet the above defined recombinant or hybrid sequence will be expressed at high levels constitutively or only or mostly in certain organs of the cultivated plants depending on which plant promoter has been chosen to control its expression. In the case of seed-specific promoters the hybrid storage protein will be produced mostly in the seeds.

It will be understood that the "heterologous nucleic acid insert" defined above consists of an insert which contains nucleotide sequences which at least in part, may be foreign to the natural nucleic acid encoding the precursor of the 2S albumins of the plant cells concerned and encode the appropriate amino acids. Most generally the segment encoding polypeptide containing said appropriate amino acids will itself be foreign to the natural nucleic acid encoding the precursor of said storage protein. Nonetheless, the term "heterologous nucleic acid insert" also extends to an insert containing a segment as above-defined normally present in the genetic patrimony or information of said plant cells, the "heterologous" character of said insert then relating to the different genetic environment which surrounds said insert.

In the preceding definition of the process according to the invention, the so-called "nonessential region" of the relevant sequence of said nucleic acid encoding the precursor consists of a region whose nucleotide sequence can be modified either by insertion into it of the above defined insert or by replacement of at least part of said nonessential region by said insert, yet without disturbing the stability and correct processing of said hybrid storage protein as well as its transport into the above-said protein bodies. Sequences consisting of said insert or replacement and representing the coding region for a polypeptide containing appropriate amino acids can either be put in as synthetic oligomers or as restriction fragments isolated from other genes, as taught by Brown, 1986. The total length of the hybrid storage protein may be longer or shorter than the total length of the non-modified 2S albumin.

With respect to the choice of the region to be modified, the present invention is clearly distinguishable from other work which has been done in this field. Reference is made to DD-A-240911 patent from the Akademie der Wissenschaften der DDR where legumin genes from *Vicia faba*, (glutine and prolamine) were modified in vitro with sequences encoding methionine. As the place of insert a natural occurring PstI site has been chosen. At the EMBO workshop "Plant storage protein genes" (Breisach, FRG, September 1986) the authors presented their work and informed the audience that plant transformation experiments had just been started with the modified gene. No further results have yet been published.

Reference is also made to patent application WO-A-87/07299 and corresponding publication of Radke et al., 1988. These papers describe the modification of the napin gene, which encodes the 2S albumin of *Brassica napus*, by a nucleotide sequence encoding nine amino acid residues including 5 consecutive methionines. The region of modification is a naturally occurring SstI site within the region encoding the mature protein. Such a modification would result in a insertion directly adjacent to a cysteine residue and moreover in a region between two cysteines, namely the 4th and the 5th cysteines of the mature protein which correspond with the 2nd and 3rd cysteines of the large subunit, whose length is strongly conserved (see above). We believe such a modification is likely to disrupt normal folding and stability of the 2S albumin (see also EP 87 402 348.4). Moreover, the above cited references provide no evidence that the desired modified 2S albumin was successfully synthesized, correctly processed or correctly targeted.

In the present invention the precursor-coding nucleic acid referred to above may of course originate from the same plant species as that which is cultivated for the purpose of the invention. It may however originate from another plant species, in line with the teachings of Beachey et al., 1985 and Okamuro et al., 1986, supra.

In a similar manner the plant promoter may originate from the same plant species or from another, subject in the last instance to the capability of the host plant's polymerases to recognize it. It may act constitutively or in a tissue-specific manner, such as, but not limited to, seed-specific promoters.

Regions such as the ones at the end of the small subunit, at the beginning or end of the large subunit, show differences of such a magnitude that they can be held as presumably having no substantial impact on the final properties of the protein. The extreme carboxyl terminus of the small subunits and the amino terminus of the large subunit may, however, be involved in the processing of the internal processed fragment. A region which does not seem essential, consists of the middle position of the region located in the large subunit, between the sixth and the seventh cysteine of the mature protein, but not immediately adjacent and at least 3 amino acids separated from said cysteines. Thus in addition to the absence of similarity at the level of the amino acid residues, there appears a difference in length which makes that region eligible for substitutions in the longest 2S albumins and for addition of amino acids in the shortest 2S albumins or for elongation of both. The same should be applicable at approximately of the end of the first third part of the same region between said sixth and seventh cysteine see the sequence of *R. communis* which is much shorter at that region than the corresponding regions of the other exemplified 2S proteins. It is of course realized that caution must be exercised with hypotheses based on arbitrary choices as concerns the bringing into line of similar parts of proteins which elsewhere exhibit substantial differences. Nevertheless such comparisons have proven in other domains of genetics to provide the man skilled in the art with appropriate guidance to reasonably infer from local structural differences, on the one hand, and from local similarities, on the other hand, in similar proteins of different sources, which parts of such proteins can be modified and which parts cannot, when it is sought to preserve some basic properties of the non modified protein in the same protein yet locally modified by a foreign or heterologous sequence.

The choice of the adequate nonessential regions to be used in the process of the invention will also depend on the length of the polypeptide containing the appropriate amino acids. Basically the method of the invention allows the modification of said 2S albumins by the insertion and/or partial substitution into the precursor nucleic acid of sequences encoding up to 100 amino acids.

When the complete protein sequence of the region to be inserted into a 2S albumin has been determined, the nucleotide sequence to encode said protein sequence must be determined. It will be recognized that while perhaps not absolutely necessary the codon usage of the encoding nucleic acid should where possible be similar to that of the gens being modified. The person skilled in the art will have access to appropriate computer analysis tools to determine said codon usage. Any appropriate genetic engineering technique may be used for substituting the insert for part of the selected precursor-coding nucleic acid or for inserting it in the appropriate region of said precursor-coding nucleic acid. The general in vitro recombination techniques followed by cloning in bacteria can be used for making the chimeric genes. Site-directed mutagenesis can be used for the same purposes as further exemplified hereafter. DNA recombinants, e.g. plasmids suitable for the transformation of plant cells can also be produced according to techniques disclosed in current technical literature. The same applies finally to the production of transformed plant cells in which the hybrid storage protein encoded by the relevant parts of the selected precursor-coding nucleic acid can be expressed. By way of example, reference can be made to the published European application no. 116 718 or to International application WO 84/02913 and, which disclose appropriate techniques.

When designing the sequences rich in appropriate amino acids, care must be taken that the resulting peptide containing said appropriate amino acids does not influence the stability of the modified 2S albumin. Certain insertions may indeed disrupt the structure of the protein. For example, long stretches of methionines may result in rod shaped helices which would result in instabilities due to disruption of normal folding patterns. Thus such sequences must occasionally include amino acids which interrupt the helical structure.

The procedures which have been disclosed hereabove apply to the adequate modification of the nonessential region of any 2S albumins by an heterologous insert containing a DNA sequence encoding a peptide containing appropriate amino acids with nutritional properties and then to the transformation of the relevant plants with the chimeric gens obtained for the production of a hybrid protein containing the sequence of said peptide in the cells of the relevant plant. Needless to say that the person skilled in the art will in all instances be able to select among existing techniques those which would best fulfill the needs at the level of each step in the production of such modified plants, to achieve the best production yields of said hybrid storage protein.

For instance the following process can be used in order to exploit the capacity of a 2S albumin, to be used as a suitable vector for the production of plants with increased nutritional value, by inserting in said 2S albumins nucleotide codons encoding methionine and/or lysine and/or tryptophan and/or threonine and/or phenylalanine and/or leucine and/or valine and/or isoleucine when the corresponding precursor-coding nucleic acid has been sequenced. Such process then comprises:

1) locating and selecting one of said relevant sequences of the precursor-coding nucleic acid which comprises a nonessential region encoding a peptide sequence which can be modified by substituting an insert for part of it or by inserting of said insert into it, which modification is compatible with the conservation of the configuration of said 2S albumins and this preferable by determining the relative positions of the codons which encode the successive cysteine residues in the mature protein or protein subunits of said 2S albumins and identifying the corresponding successive nucleic acid regions located upstream of, between, and downstream of said codons with in said sub-sequences of the precursor-coding nucleic acid and identifying in said successive regions those parts which undergo variability in either amino acid sequence or length or both from one plant species to another as compared with those other regions which do exhibit substantial conservation of amino acid sequence in said several plant species, one of said nucleotide regions being then selected for the insertion therein of the nucleic acid insert as described hereunder.

An alternative would consist of studying any 3-D structures which may become available in the future.

2) inserting a nucleic acid insert in the selected region of said precursor nucleic acid in appropriate reading frame relationship with the non-modified parts of said relevant sequence, which insert includes a determined segment encoding a peptide containing all or part of the above mentioned appropriate amino acids.

3) inserting the modified precursor-coding nucleic acid obtained in a plasmid suitable for the transformation of plant cells which can be regenerated into full seed-forming plants, wherein said insertion is brought under the control of regulation elements, particularly a plant promoter capable of providing for the expression of the open reading-frames associated therewith in said plants;

4) transforming a culture of such plant cells with such modified plasmid;

5) assaying the expression of the chimeric gene encoding the hybrid storage protein and, when achieved;

6) regenerating said plants from the transformed plant cells obtained and growing said plants to maturity.

In the case the chimeric gene is under the control of a seed specific promotor, growing the transformed plants to seeds must precede step 5)

Hence, an embodiment as described under 1) of the invention hereabove provides that in having the hybrid 2S albumins in a plant, it will pass the plant protein disulfide isomerase during membrane translocation, thus increasing the chances that the correct disulfide bridges are formed in the hybrid precursor as in its normal precursor situation.

The invention further relates to the recombinant nucleic acids themselves for use in the process of the invention; particularly to the recombinant precursor encoding nucleic acid defined in the context of said process;

recombinant nucleic acids containing said modified precursor encoding nucleic acid under the control of a plant promoter, whether the latter originates from the same DNA as that of said precursor coding nucleic acid or from another DNA of the same plant from which the precursor encoding nucleic acid is derived, or from a DNA of another plant, or from a non-plant organism provided that it is capable of directing gene expression in plants.

vectors, more particularly plant plasmids e.g., Ti-derived plasmids modified by any of the preceding recombinant nucleic acids for use in the transformation of the above plant cells.

The invention also relates to the regenerable source of the hybrid 2S albumin, which is formed in the cell of a seed-forming-plant, which plant cells are capable of being regenerated into the full plant or seeds of said seed-forming plants wherein said plants or seeds have been obtained as a result of one or several generations of the plants resulting from the regeneration of said plant cells, wherein further the DNA supporting the genetic information of said plant cells or seeds comprises a nucleic acid or part thereof, including the sequences encoding the signal peptide, which can be transcribed in the mRNA corresponding to the precursor of a 2S albumin of said plant, placed under the control of a plant specific promoter, and wherein said nucleic acid sequence contains a relevant modified sequence encoding the mature 2S storage protein or one of the several sub-sequences encoding for the corresponding one or several sub-units of said mature 2S albumins, wherein further the modification of said relevant sequence takes place in one of its nonessential regions and consists of a heterologous nucleic acid insert forming an open-reading frame in reading phase with non modified parts which surround said insert in the relevant sequence, wherein said insert consists of a nucleotide segment encoding a peptide containing methionine and/or lysine and/or tryptophan and/or threonine and/or phenylalanine, and/or leucine and/or valine and/or isoleucine.

It is to be considered that although the invention should not be deemed as being limited thereto, the nucleic inserts encoding the above mentioned appropriate amino acids will in most instances be man-made synthetic oligonucleotides or oligonucleotides derived from procaryotic or eucaryotic genes or from cDNAs derived of procaryotic or eucaryotic RNAs, all of which shall normally escape any possibility of being inserted at the appropriate places of the plant cells or seeds of this invention through biological processes, whatever the nature thereof. In other words, these inserts are "non plant variety specific", specially in that they can be inserted in different kinds of plants which are genetically totally unrelated and thus incapable of exchanging any genetic material by standard biological processes, including natural hybridization processes.

Thus the invention further relates to the seed forming plants themselves which have been obtained from said transformed plant cells or seeds, which plants are characterized in that they carry said hybrid precursor-coding nucleic acids associated with a plant promoter in their cells, said inserts however being expressed and the corresponding hybrid protein produced in the cells of said plants.

There follows an outline of a preferred method which can be used for the modification of a 2S albumin gene and its expression in the seeds obtained from the transgenic plants. The outline of the method given here is followed by a specific example. It will be understood from the person skilled in the art that the method can be suitably adapted for the modification of other 2S albumin genes.

1. Replacement or supplementation of the hypervariable region of the 2S albumin gene by a sequence encoding peptide containing appropriate amino acids which possess nutritional properties.

Either the cDNA or the genomic clone of the 2S albumin can be used. Comparison of the sequences of the hypervariable regions of the genes in FIG. 2 shows that they vary in length. Therefore if the sequence encoding a peptide containing the appropriate amino acids is short and a 2S albumin with a relatively short hypervariable region is used, said sequence of interest can be inserted. Otherwise part of the hypervariable region is removed, to be replaced by the insert containing a larger segment or sequence encoding the peptide containing the appropriate amino acids. In either case the modified hybrid 2S albumin may be longer than the native one. In either case two standard techniques can be applied; convenient restriction sites can be exploited, or mutagenesis vectors (e.g. Stanssens et al. 1987) can be used. In both cases, care must be taken to maintain the reading frame of the message.

The sequence encoding the signal peptide of the precursor of the storage protein used either belongs to this precursor or can be a substitute sequence coding for the signal peptide or peptides of an heterologous storage protein.

2. The altered 2S albumin coding region is placed under the control of a plant promoter. Preferred promoters include the strong constitutive exogeneous plant promoters such as the promoter from cauliflower mozaic virus directing the 35S transcript (Odell, J. T. et al., 1985), also called the 35S promoter; the 35S promoter from the CAMV isolate Cabb-JI (Hull and Howell, 1987), also called the 35S3 promoter; the bidirectional TR promoter which drives the expression of both the 1'and the 2' genes of the T-DNA (Velten et al., 1984). Alternatively a promoter can be utilized which is not constitutive but specific for one or more tissues or organs of the plant. By way of example such promoters may be the light inducible promoter of the ribulose-1, 5-bis-phosphate carboxylase small subunit gene (U.S. patent application Ser. No. 821,582), if the expression is desired in tissue with photosynthetic activity, or such promotor may be seed specific promoters.

A seed specific promoter is used in order to ensure subsequent expression in the seeds only. This may be of particular use, since seeds constitute an important food or feed source. Moreover, this specific expression avoids possible stresses on other parts of the plant. In principle the promoter of the modified 2S albumin can be used. But this is not necessary. Any other promoter serving the same purpose can be used. The promoter may be chosen according to its level of efficiency in the plant species to be transformed. In the examples below the 2S albumin promoter from the 2S albumin gene from Arabidopsis is used, which constitutes the natural promotor of the 2S albumin gene which is modified in said examples. Needless to say that other seed specific promotors may be used, such as the conglycinine promotor from soybean. If a chimeric gens is so constructed, a signal peptide encoding region must also be included, either from the modified gens or from the gens whose promotor is being used. The actual construction of the chimeric gens is done using standard molecular biological techniques described in Maniatis al., 1982. (see example).

3. The chimeric gens construction is transferred into the appropriate host plant.

When the chimeric or modified gens construction is complete it is transferred in its entirety to a plant transformation vector. A wide variety of these, based on disarmed (non-oncogenic) Ti-plasmids derived from *Agrobacterium tumefaciens*, are available, both of the binary and cointegration forms (De Blaere et al., 1987). A vector including a selectable marker for transformation, usually antibiotic resistance, should be chosen. Similarly, the methods of plant transformation are also numerous, and are fitted to the individual plant. Most are based on either protoplast transformation (Marion et al., 1979) or formation of a small piece of tissue from the adult plant (Horsch et al., 1985). In the example below, the vector is a binary disarmed Ti-plasmid vector, the marker is kanamycin resistance, and the leaf disc method of transformation is used.

Calli from the transformation procedure are selected on the basis of the selectable marker and regenerated to adult plants by appropriate hormone induction. This again varies with the plant species being used. Regenerated plants are then used to set up a stable line from which seeds can be harvested.

Further characteristics of the invention will appear in the course of the non-limiting disclosure of specific examples, particularly on the basis of the drawings in which:

BRIEF DESCRIPTION OF THE DRAWINGS

FIG. 1 shows diagrammatically the organization of 2S albumin precursors.

Figure 2B:
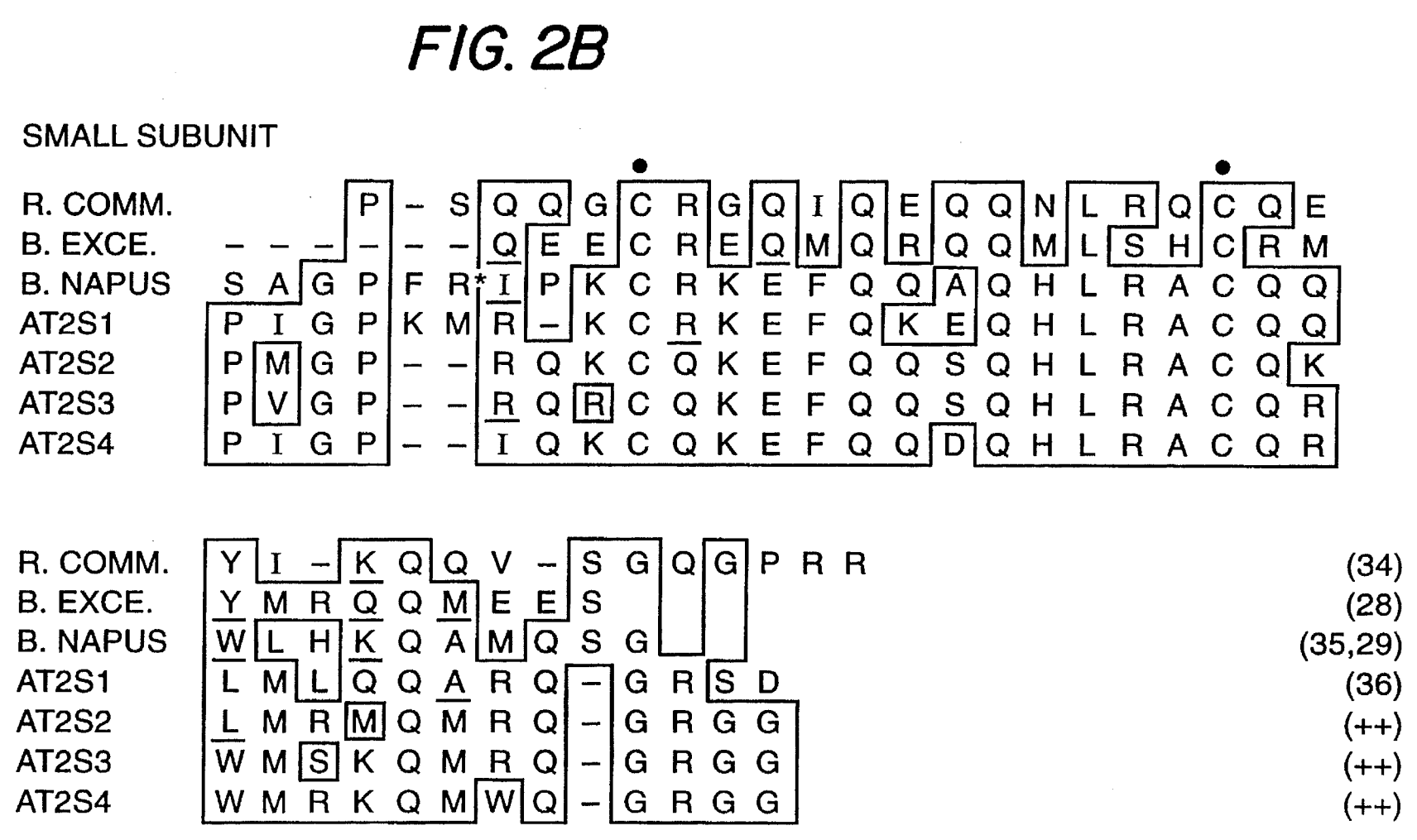

FIG. 2 shows a comparison of 2S albumin precursor protein sequences.

FIG. 4 represents the sequence of 1 kb fragment containing the *Arabidopsis thaliana* 2S albumin gene and shows related elements. The NdeI site is underlined.

FIG. 5 provides the protein sequence of the large subunit of the above Arabidopsis 2S protein together with related oligonucleotide sequences.

EXAMPLE 1

As a first example of the method described, a procedure is given for the production of transgenic plant seeds with increased nutritional value by having inserted into their genome a modified 2S albumin protein from *Arabidopsis thaliana* having deleted its hypervariable region and replaced by way of example by a methionine rich peptide having 7 amino acids with the following sequence :I M M M M R M. A synthetic oligomer encoding said peptide is substituted for essentially the entire part of the hypervariable region in a genomic clone encoding the 2S albumin of *Arabidopsis thaliana*. Only a few amino acids adjacent to the sixth and seventh cysteine residues remained. This chimeric gene is under the control of its natural promoter and signal peptide. The process and constructions are diagrammatically illustrated in FIG. 6A, 6B and 7. The entire construct is transferred to tobacco, *Arabidopsis thaliana* and *Brassica napus* plants using an *Agrobacterium* mediated transformation system. *Brassica napus* is of particular interest, since this crop is widely used as protein source for animal feed.

Plants are regenerated, and after flowering the seeds are collected and the methionine content compared with untransformed plants.

1. Cloning of the *Arabidopsis thaliana* 2S Albumin Gene

The *Arabidopsis thaliana* gene has been cloned according to the description in Krebbers et al., 1988. The plasmid containing said gens is called pAT2S1. The sequence of the region containing the gene, which is called AT2S1, is shown in FIG. 4.

Figure 8:
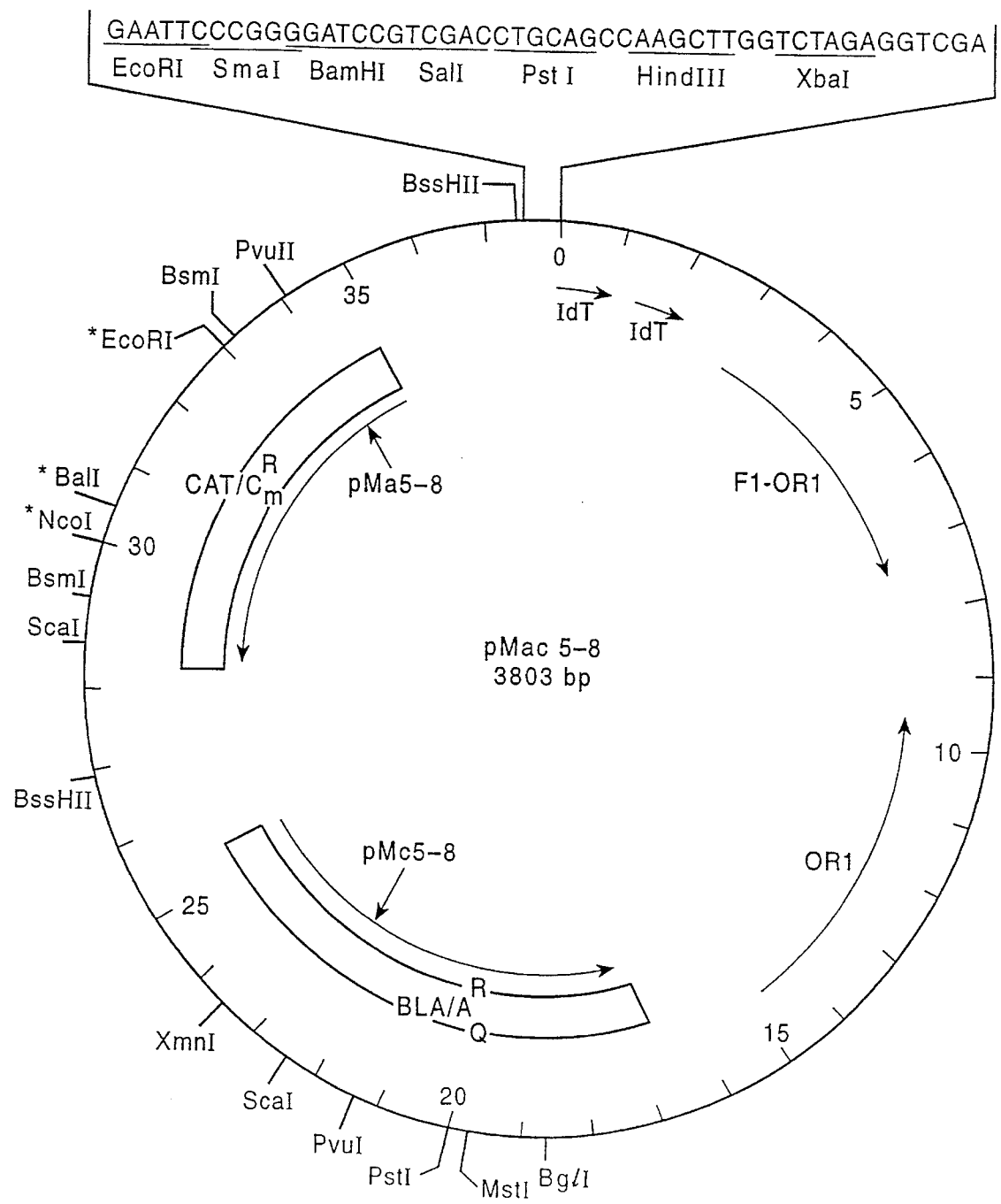
FIG. 8 shows the restriction sites and genetic map of a plasmid suitable for the performance of the above site-directed mutagenesis.

2. Deletion of the Hypervariable Region of AT2S1 Gene and Replacement by an AccI Site Part of the hypervariable region of AT2S1 is replaced by the following oligonucleotide:

5'- CCA ACC TTG AAA GGT ATA CAC TTG CCC AAC -3'
30-mer
     P   T   L   K   G   I   H   L   P   N in which the underlined sequences represent the AccI site and the surrounding ones sequences complementary to the coding sequence of the hypervariable region of the Arabidopsis 2S albumin gens to be retained. This results finally in the amino acid sequence indicated under the oligonucleotide. The deletion and substitution of part of the sequence encoding the hypervariable region of AT2S1 is done using site directed mutagenesis with the oligonucleotide as primer. The system of Stanssens et al. (1987) is used. The Stanssens et al. method is described in EP 87 402 384.4. It makes use of plasmid pMac5-8 whose restriction and genetic map and the positions of the relevant genetic loci are shown in FIG. 8. The arrows denote their functional orientation.

fdT: central transcription terminator of phage fd; F1-ORI: origin of replication of filamentous phage f1; ORI: ColE1-type origin of replication; BLA/Ap$^R$: region coding for B-lactamase; CAT/Cm$^R$: region coding for chloramphenicol acetyl transferase. The positions of the amber mutations present in pMc5-8 (the bla-am gene do not contain the ScaI site) and pMc5-8(cat-am; the mutation eliminating the unique PvuII site) are indicated. Suppression of the cat amber mutation in both supE and supF hosts results in resistance to at least 25 ug/ml Cm. pMc5-8confers resistance to ±20 ug/ml and 100 ug/ml Ap upon amber-suppression in supE and supF strains respectively. The EcoRI, BalI and NcoI sites present in the wild-type cat gene (indicated with an asterisk) have been removed using mutagenesis techniques.

Figure 9A:
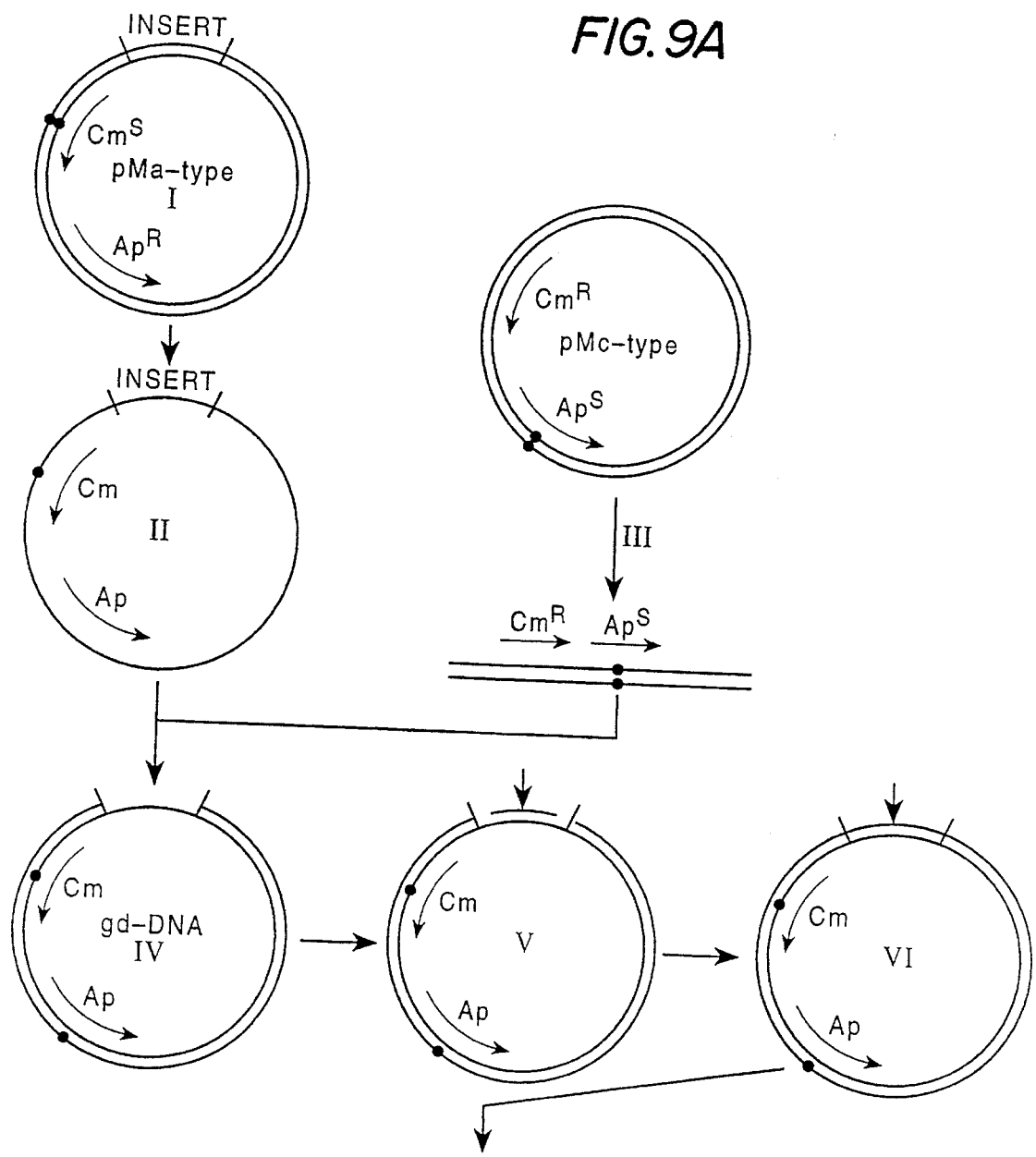
FIG. 9 shows diagrammatically the different steps of the site-directed mutagenesis procedure of Stanssens et al (1987) as generally applicable to the modification of nucleic acid at appropriate places.
Figure 9B:
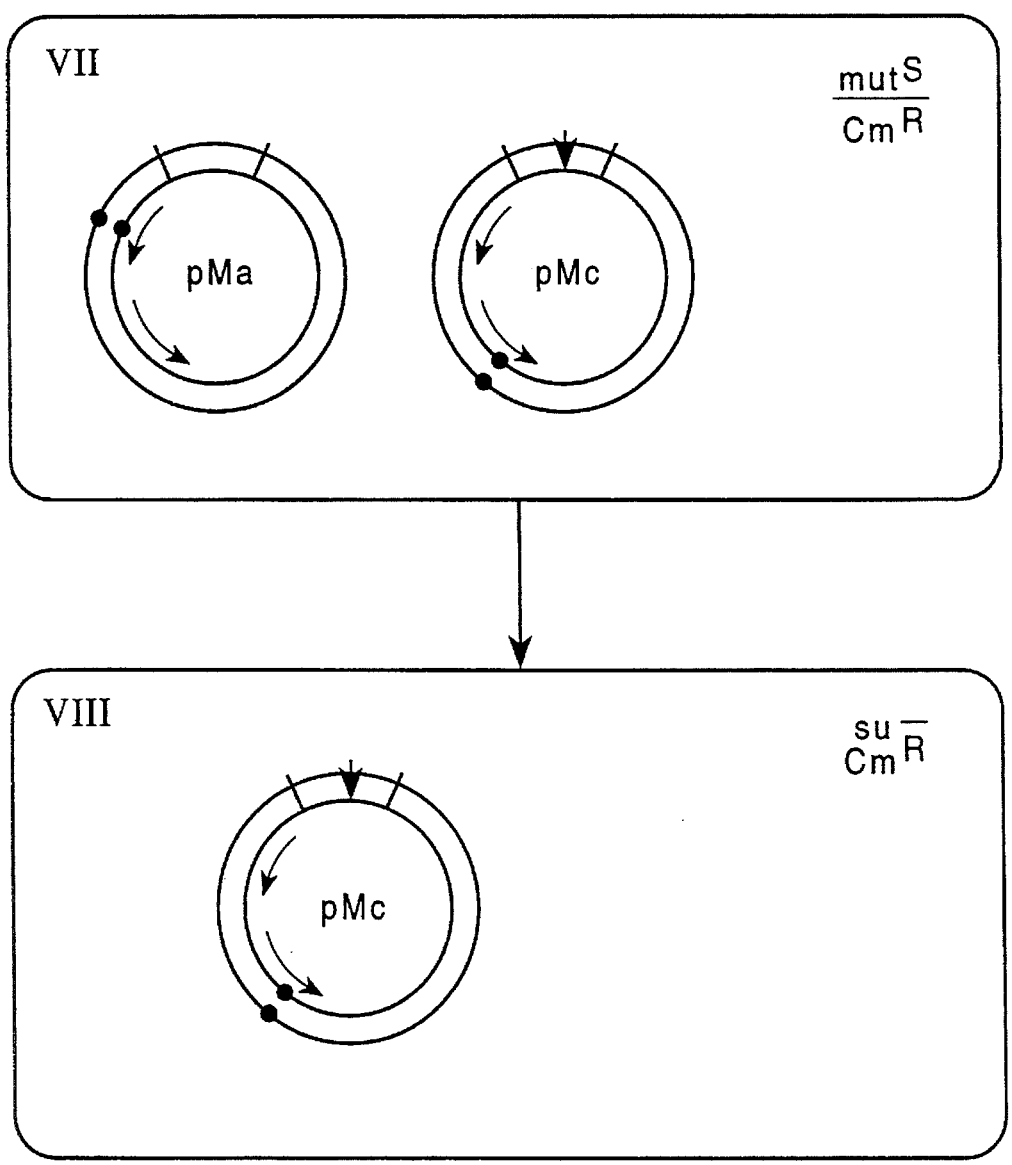

Essentially the mutagenesis round used for the above mentioned substitution was run as follows. Reference is made to FIG. 9, in which the amber mutations in the Ap and Cm selectable markers are shown by closed circles. The symbol represents the mutagenic oligonucleotide. The mutation itself is indicated by an arrowhead.

The individual steps of the process are as follows:

Cloning of the HindIII fragment of pAT2S1 containing the coding region of the AT2S1 gene into pMa5-8 (I). This vector carries on amber mutation in the Cm$^R$ gene and specifies resistance to ampicillin. The resulting plasmid is designated pMacAT2S1 (see FIG. 6A step 1).

Preparation of single stranded DNA of this recombinant (II) from pseudovital particles.

Preparation of a HindIII restriction fragment from the complementary pMc type plasmid (III). pMc-type vectors contain the wild type Cm$^R$ gene-while an amber mutation is incorporated in the Ap resistance marker.

Construction of gap duplex DNA (hereinafter called gdDNA) gdDNA (IV) by in vitro DNA/DNA hybridization. In the gdDNA the target sequences are exposed as single stranded DNA. Preparative purification of the gdDNA from the other components of the hybridization mixture is not necessary.

Annealing of the 30-met synthetic oligonucleotide to the gdDNA (V).

Filling in the remaining single stranded gaps and sealing of the nicks by a simultaneous in vitro Klenow DNA polymerass I / DNA ligase reaction (VI).

Transformation of a mutS host, i.e., a strain deficient in mismatch repair, selecting for Cm resistance. This results in production of a mixed plasmid progeny (VII).

Elimination of progeny deriving from the template strand (pMa-type) by retransformation of a host unable to suppress amber mutations (VIII). Selection for Cm resistance results in enrichment of the progeny derived from the gapped strand, i.e., the strand into which the mutagenic oligonucleotide has been incorporated.

Screening of the clones resulting from the retransformation for the presence of the desired mutation. The resulting plasmid containing the deleted hypervariable region of AT2S1 is called pMacAT2S1C40 (see FIG. 6A step 2).

3. Insertion of Sequences Rich in Methionine Codons Into the AT2S1 Gene Whose Sequences Encoding the Hypervariable Region Have Been Deleted As stated above when the sequences encoding most of the hypervariable loop were removed an AccI site was inserted in its place. The sequences of interest will be inserted into this AccI site, but a second AccI site is also present in the HindIII fragment containing the modified gene. Therefore the NdeI-HindIII fragment containing the modified gene is sub-cloned into the cloning vector pBR322 (Bolivar, 1977) also cut with NdeI and HindIII. The position of the NdeI site in the 2S albumin gene is indicated in FIG. 4. The resulting subclone is designated pBRAT2S1 (FIG. 6A, step 3).

In principle any insert desired can be inserted into the AccI site in pBRAT2S1. In the present example said insert encodes the following sequence: I.M.M.M.M.R.M. Therefore complementary oligonucleotides encoding said peptide are synthesized taking into account the codon usage of AT2S1 and ensuring the ends of the two complementary oligonucleotides are complementary to the staggered ends of the AccI site, as shown here:

```
5' GT ATA ATG ATG ATG ATG CGC ATG ATAC 3'
3' CA TAT TAC TAC TAC TAC GCG TAC TATG 5'
```

Figure 3:
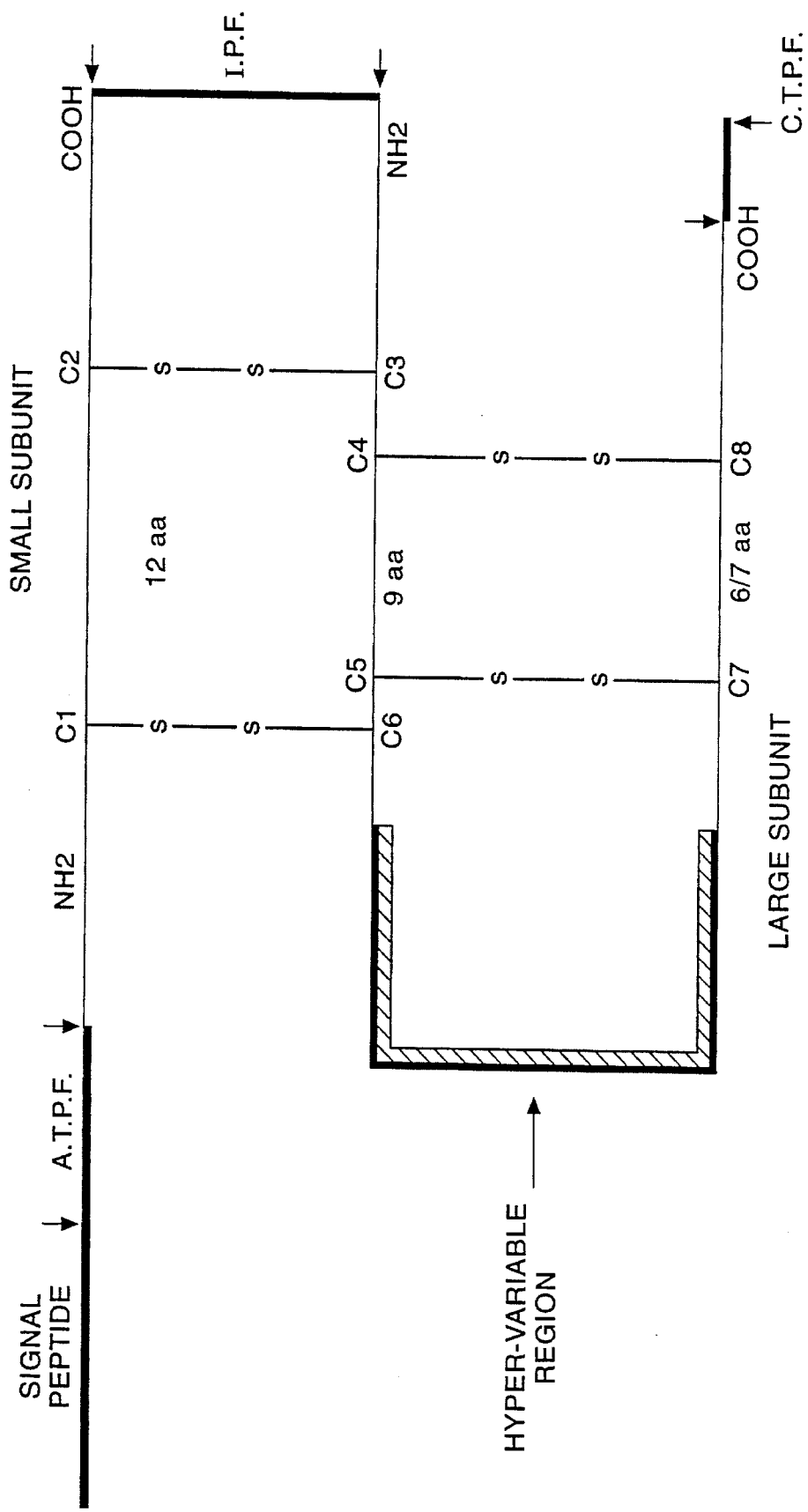
FIG. 3 represents a hypothetical model of the 2S albumin of *Arabidopsis thaliana*.
Figure 6:
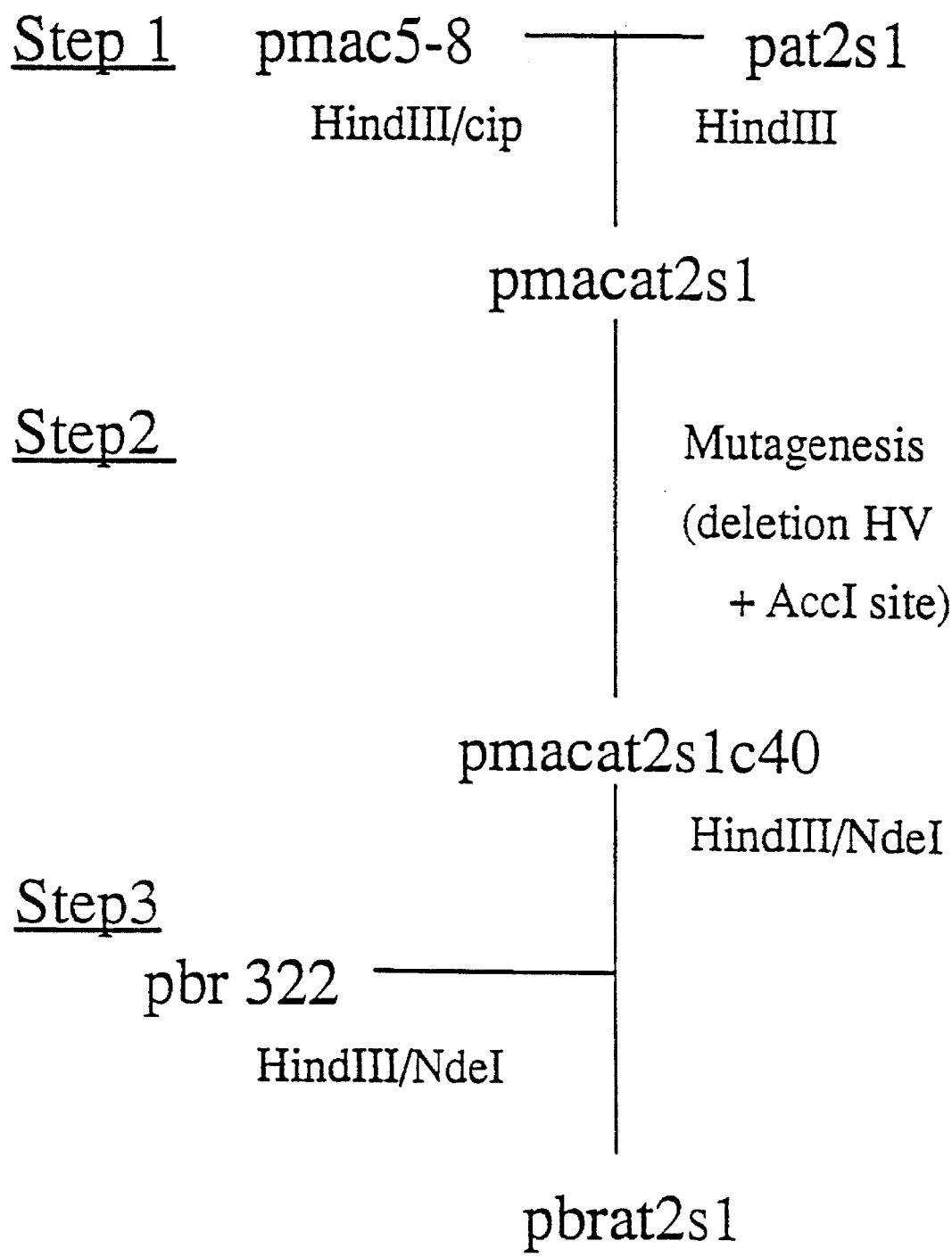
FIG. 6A (1) and (2) shows diagrammatically the successive phases of the construction of a chimeric 2S albumin *Arabidopsis thaliani* gene including the deletion of practically all parts of the hypervariable region and its replacement by a AccI site, the insertion of DNA sequences rich in methionine codons, given by way of of example in the following disclosure, in the AccI site, particularly through site-directed mutagenesis and the cloning of said chimeric gene in plant vector suitable for plant transformation.
FIG. 6B (1) and (2) shows diagrammatically the protein sequence of the large subunit of several Arabdopsis 2S albumins and indicates the region removed from the genes encoding said 2S albumins, and shows diagrammatically there an AccI site has been created and how oligonucleotides rich in methionine codons are inserted into said AccI site in such a way that the open reading frame is maintained.

The details of this insertion, showing how the reading frame is maintained, are shown in FIG. 6B. The two oligonucleotides are annealed and ligated with pBRAT2S1 digested with AccI ( FIG. 6A, step 4). The resulting plasmid is designated pAD4.

4. Reconstruction of the Complete Modified AT2S1 gene with Its Natural Promoter

The complete chimeric gene is reconstructed as follows (see FIG. 6A): The clone pAT2S1Bg contains a 3.6 kb BglII fragment inserted in the cloning vector pJB65 (Botterman et al., 1987) which encompasses not only the 1.0 kb HindIII fragment containing the coding region of the gene AT2S1 but sufficient sequences upstream and downstream of this fragment to contain all necessary regulatory elements for the proper expression of the gene. This plasmid is cut with HindIII and the 5.2 kb fragment (i.e., that portion of the plasmid not containing the coding region of AT2S1) is isolated. The clone pAT2S1 is cut with HindIII and NdeI and the resulting 320 bp HindIII-NdeI fragment is isolated. This fragment represents the one removed from the modified 2S albumin in the construction of pBRAT2S1 (step 3 of FIG. 6A) in order to allow the insertion of the oligonucleotides in step 4 of FIG. 6A to proceed without the complications of an extra AccI site. These two isolated fragments are then ligated in a three way ligation with the NdeI-HindIII fragment from pAD4 (FIG. 6A, step 5) containing the modified coding sequence. Individual tranformants can be screened to check for appropriate orientation of the reconstructed HindIII fragment within the BglII fragment using any of a number of sites. The resulting plasmid, pAD17, consists of a 2S albumin gene modified only in the hypervariable region, surrounded by the same flanking sequences and thus the same promoter as the unmodified gene, the entirety contained on a BglII fragment.

5. Transformation of Plants

Figure 10:
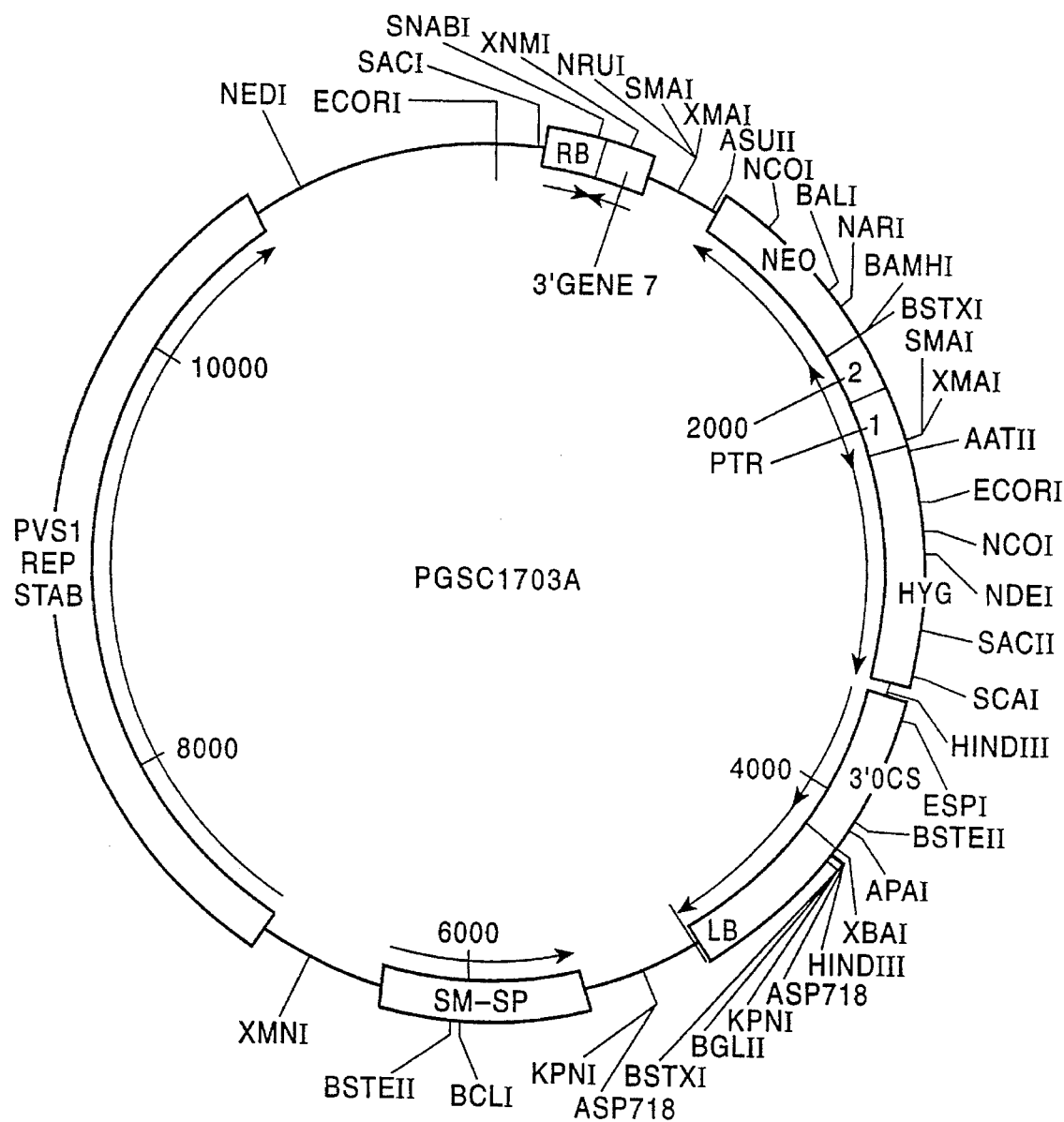
FIG. 10 gives the restriction map of pGSC1703A.

The BglII fragment containing the chimeric gene is inserted into the BglII site of the binary vector pGSC1703A (FIG. 10) (see also FIG. 6A step 6). The resultant plasmid is designated pTAD12. Vector pGSC1703A contains functions for selection and stability in both E. coli and A. tumefaciens as well as a T-DNA fragment for the transfer of foreign DNA into plant genomes (Deblaere et al., 1987). It further contains the hi-directional TR promotor (Velten et al., 1984) with the neomycin phosphotransferase protein coding region (neo) and the 3' end of the ocs gene on one side, and a hygromycin transferase gene on the other side, so that transformed plants are both kanamycin and hygromycin resistant. This plasmid does not carry an ampicillin resistance gene, so that carbenicillin as well as claforan can be used to kill Agrobacterium after the infection step. Using standard procedures (Deblaere et al., 1987), pTAD12 is transferred to the Agrobacterium strain C58ClRif carrying the plasmid pMP90 (Koncz and Schell, 1986). The latter provides in trans the vir gene functions required for successful transfer of the T-DNA region to the plant genome. This Agrobacterium is then used to transform plants. Tobacco plants of the strain SR1 are transformed using standard procedures (Deblaere et al., 1987). Calli are selected on 100 ug/ml kanamycin, and resistant calli used to regenerate plants.

The techniques for transformation of Arabidopsis thaliana and Brassica napus are such that exactly the same construction, in the same vector, can be used. After mobilization to Agrobacterium tumefaciens as described hereabove, the procedures of Lloyd et al., (1986) and Klimaszewska et al. (1985) are used for transformation of Arabidopsis and Brassica respectively. In each case, as for tobacco, calli can be selected on 100 ug/ml kanamycin, and resistant calli used to regenerate plants. In the case of all three species at an early stage of regeneration the regenerants are checked for transformation by inducing callus from leaf on media supplemented with kanamycin (see also point 6).

6. Screening and Analysis of Transformed Plants

In the case of all three species, regenerated plants are grown to seed. Since different transformed plants can be expected to have varying levels of expression ("position effects" Jones et al, 1985), more than one tranformant must initially be analyzed. This can in principle be done at either the RNA or protein level; in this case seed RNA was prepared as described (Beachy et al., 1985) and northern blots carried out using standard techniques (Thomas et al., 1980). Since in the case of both Brassica and Arabidopsis the use of the entire chimeric gene would result in cross hybridization with endogeneous genes, oligonucleotide probes complementary to the insertion within the 2S albumin were used I the same probe as used to make the construction can be used. For each species, 1 or 2 individual plants were chosen for further analysis as discussed below.

First the copy number of the chimeric gene is determined by preparing DNA from leaf tissue of the transformed plants (Dellaporta et al., 1983) and probing with the oligonucleotide used above.

The methionine content of the seeds is analyzed using known methods (Joseph and Marsden, 1986; Gehrke et al., 1985; Elkin and Griffith, 1985 (a) and (b)).

EXAMPLE II

As a second example of the method described, the same procedure is followed for the production of transgenic plant seeds with increased nutritional value by having inserted into their genome a modified 2S albumin protein from *Arabidopsis thaliana* having deleted its hypervariable region and replaced by way of example by a methionine rich peptide having 24 amino acids with the following sequence:

I M M M Q P R G D M M M I M M M Q P R G M M M

All different steps going from constructs to transformants as disclosed for example I are executed with the only difference that in step 3 the following oligonucleotide has been synthesized and inserted into pBrAT2S1

5' GT ATA ATG ATG ATG CAA CCA AGG GGC GAT ATG ATG ATG ATA
ATG ATG ATG CAA CCA AGG GGC GAT ATG ATG ATG ATA C -3'
3' CA TAT TAC TAC TAC GTT GGT TCC CCG GTA TAC TAC TAC TAT
TAC TAC TAC GTT GGT TCC CCG CTA TAC TAC TAC TAT G -5'

Figure 7:
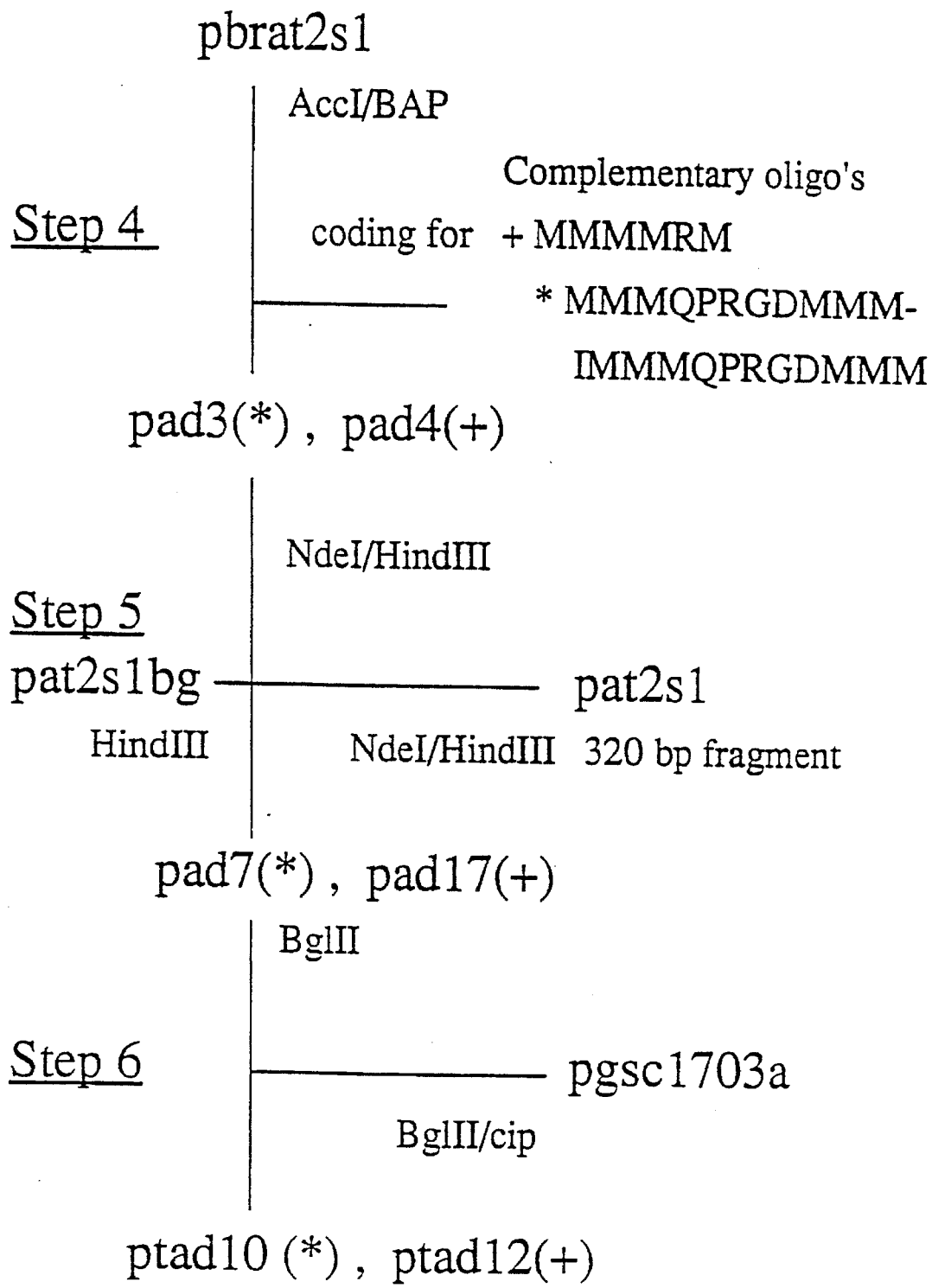
FIG. 7 diagrammatically compares the protein sequences of the large subunits of the unmodified 2S albumin in which most of the hypervariable region has been deleted, and those of the modified 2S albumins. The resulting number of methionine residues are indicated.

The relevant plasmids are indicated in FIG. 6A, details of the insertion in FIG. 6B and resulting amino acid sequence of the hybrid subunit shown in FIG. 7. The relevant plasmids as indicated in FIG. 6A are pAD3, pAD7 and pTAD10.

The examples have thus given a complete illustration of how 2S albumin storage proteins can be modified to incorporate therein an insert encoding a methionine rich polypeptide followed by the transformation of plant cells such as tobacco cells, Arabidopsis cells and Brassica napus cells with an appropriate plasmid containing the corresponding modified precursor nucleic acid, the regeneration of the transformed plant cells into corresponding plants, the culture thereof up to the seed forming stage, the recovery of the seeds and finally the analysis of the methionine content of said seeds compared with the seeds of corresponding non transformed plants.

It goes without saying that the invention is not limited to the above examples. The person skilled in the art will in each case be able to choose the desired combination of appropriate amino acids to be inserted into the hypervariable region of the 2S storage protein, in function of the plant he wants to improve with regard to its nutritional value and in function of the desired application of the modified plant.

There follows a list of bibliographic references which have been referred to in the course of the present disclosure to the extent when reference has been made to known methods for achieving some of the process steps referred to herein or to general knowledge which has been established prior to the performance of this invention. All of the said articles are incorporated herein by reference.

It is further confirmed that plasmid pAT2S1 has been deposited with the DSM on 4879 on Oct. 7, 1988 plasmids pMa5-8 has been deposited with the DSM on 4567 and pMc on 4566 on May 3, 1988 plasmid pAT2S1Bg has been deposited with the DSM on 4878 on Oct. 7, 1988 plasmid pGSC1703a has been deposited with the DSM on 4880 on Oct. 7, 1988 nowithstanding the fact that they all consist of constructs that the person skilled in the art can reproduce from available genetic material without performing any inventive work.

REFERENCES

Altenbach, S. B., Pearson, K. W., Leung, F. W., Sun, S. S. M (1987) Plant Mol. Biol. 8, 239–250.

Ampe C., Van Damme, J., de Castro, L. A. B., Sampaio, M. J. A. M., Van Montagu, M. and Vandekerckhove, J. (1986) Eur. J. Biochem. 159, 597–604.

Beachy, R. N., Chen, Z.-L., Horsch, R. B., Rogers, S. G., Hoffman, N. J. and Fraley, R. T. (1985) EMBO J. 4, 3047–3053.

Bergman, L. W. and Kuehl, W. N. (1979) J. Biol. Chem. 254, 5690–5694.

Blobel, (1980) Proc. Natl. Acad. Sci. 77, 1496–1500.

Bolivar, F., Rodriguez, R. L., Greene, P. J., Betlach, M. C., Heynecker, H. L., Boyer, H. W., Crosa, J. H. and Falkow, S. (1977) Gene 2, 95.

Botterman, J. and Zabeau, M. (1987) DNA 6, 583–591.

Brown, J. (1976) Fed. Proc. Am. Soc. Exp. Biol. 35, 2141–2144.

Brown, J. W. S., Wandelt, Ch., Maier, U., Dietrich, G., Schwall, N., and Feix, G. (1986) EMBO workshop "Plant Storage Protein Genes" Program and Abstracts page 19, Eds. J. Brown and G. Feix, University of Freiburg, 1986.

Chee, P. P., Klassy, R. C. and Slightom, J. L. (1986) Gene 41, 47–57.

Chrispeels, N. J. (1983) Planta 158, 140–152.

Craig, S. and Goodchild, D. J. (1984) Protoplasma 122, 35–44

Crouch, M. L., Tembarge, K. M., Simon, A. E. and Ferl, R. (1983) J. Mol. Appl. Gert. 2, 273–283.

De Blaere, R., Reynaerts, A., Hofte, H., Hernalsteens, J.-P., Leemans, J. and Van Montagu, M. (1987) Methods in Enzymology 153, 277–291.

De Castro, L. A. B., Lacerada, Z., Aramayo, R. A., Sampaio, M. J. A. M. and Gander, E. S. (1987) Mol. Gen. Genet. 206, 338–343.

Dellaporta S. L. ; J. ; Wood, J. and Hicks, B. (1983) Plant Molecular Biology Reports 1, 19–21.

Ellis, J. R., Shirsat, A. H., Hepher, A., Yarwood, J. N., Gatehouse, J. A., Croy, R. R. D. and Boulter, D. (1988) Plant Molecular Biology 10, 203–214.

Elkin, R. G., and Griffith, J. E. (1985a) J. Assoc. Off. Anal. Chem. 68, 1028–1032.

Elkin, R. G., and Griffith, J. E. (1985b) J. Assoc. Off. Anal. Chem. 68, 1117–1127.

Ericson, M. L., Rodin, J., Lenman, M., Glimeliums, K., Lars-Goran, J. and Rak, L. (1986) J. Biol. Chem. 261, 14 576–14 581.

Greenwood, J. S. and Chrispeels, M. J. (1985) Plant Physiol. 79, 65–71.

Gehrke, C. W., Wal 1, L. L., Absheer, J. S., Kaiser, F. E. and Zumwalt, R. W. (1985) J. Assoc. Off. Anal. Chem. 68, 811–821.

Herman, E. M., Shannon, L. M. and Chrispeels, M. J. (1986) In *Molecular Biology of Seed Storage Proteins and Lectins*, L. M. Shannon and M. J. Chrispeels Eds., American Society of Plant Physiologists.

Higgins, T. J. V. (1984) Ann. Rev. Plant Physiol. 35,191–221.

Higgins, T. J. V., Llewellyn, D., Newbigin, E. and Spencer, D. (1986) EMBO workshop "Plant Storage Protein Genes" Program and abstract page 19, Eds. J. Brown and G. Feix, University of Freiburg, 1986.

Horsch, R. B., Fry, J. E., Hoffmann, N. L., Eichholtz, D., Rogers, S. G. and Fraley, R. T. (1985) Science 227, 1229–1231.

Hoffman, L. M., Donaldson, D. D., Bookland, R., Rashka, K., Herman, E. M. (1987) EMBO J. 6, 3213–3221.

Hull and Howell (1987): Virology, 86,4821–493.

Jagodinski, L., Sargent, T., Yang, M., Glackin, C., Bonner, J. (1987) Proc. Natl. Acad. Sci. USA. 78, 3521–3525.

Jones J. D. G.; Dunsmuir, P. and Bedbrook, J. (1985) EMBO J. 4 (10), 2411–2418.

Joseph, H. and Marsden, J. (1986) "HPLC of Small Molecules—A practical approach" in: IRL Press Oxford —Washington D.C. "Amino Acids and Small Peptides" Ed.: Kim, C. K., 13–27.

Josefsson, L-G.; Lenman, M., Ericson, M. L. and Rask, L. (1987) J. Biol. Chem. 262 (25), 12196–12201.

Klimaszewska, K. and Keller, W. A. (1985) Plant Cell Tissue Organ Culture, 4, 183–197.

Krebbers, E., Herdies, L., De Clercq, A., Seurinck, J., Leemans, J., Vandamme, J., Segura, M., Gheysen, G., Van Montagu M. and Vandekerckhove, J. (1988) Plant Physiol. 87 (4), 859–866.

Koncz, C. and Schell, J. (1986) Mol. Gen. Genet. 204, 383–396.

Larkins B. A. and Hurkman,W. J. (1978) Plant Physiol. 62, 256–263.

Lloyd, A. M., Barnason, A. R., Rogers, S. G., Byrne, M. C., Fraley, R. T. and Horsh, R. B. (1986).Science 234, 464–466.

Lord, J. M. (1985). Eur. J. Biochem. 146, 403–409.

Maniatis, T., Fritsch, E. F. and Sambrook, J. (1982) *Molecular Cloning*. Cold Spring Harbor Laboratory, Cold Spring Harbor, N.Y.

Marris, C., Gallois, P., Copley, J. and Kreis, N. (1988) Plant Molecular Biology 10, 359–366.

Marton, L., Wullems, G. J., Molendijk, L. and Schilperoort, R. A. (1979) Nature, 277, 129–131.

Morinaga, T., Sakai, N., Wegmann, T., Tanaoki, T. (1983) Proc. Natl. Acad. Sci. 80, 4604–4606.

Odell, J. T., Nagy, J. and Chua, N. M. (1985) Nature 313, 810–812.

Okamuro, J. K., Jofuku, K. D. and Goldberg, R. B. (1986) Proc. Natl. Acad. Sci. USA. 83, 8240–8244.

Perlman, D. and Halvorson, H. O. (1983 ) J. Mol. Biol. 167, 391–409.

Radke, S. E., Andrews, B. M., Molony, M. M., Crouch, M. L. Kridl, J. C. and Knauf, V. C. (1988) Theor. Appl. Genet. 75, 685–694.

Roden, L. T., Miflin, B. J., Freedman, R. B. (1982) FEBS Lett. 138, 121–124.

Scofield, S. R. and Crouch, M. L. (1987)J. Biol. Chem. 262(25), 12202–12208.

Sengupta-Gopalan, C., Reicheft, N. A., Barker,, R. F., Hall, T. C. and Kemp, J. D. (1985) Proc. Natl. Acad. Sci. USA 82, 3320–3324.

Sharief, S. F. and Steven, S. -L. (1982) J. Biol. Chem. 257 (24), 14753–14795.

Slightom, J. L. and Chee, P. P. (1987) Biotechn. Adv. 5, 29–45.

Stanssens, P., McKeown, Y., Friedrich, K., and Fritz, H. J. (1987) Manual EMBO Laboratory Course; 'Directed mutagensis and protein engineering' held at Max Planck Institute Biochemie, Martinsried, W-Germany, Jul. 4–18, 1987.

Staswick, P. E. (1988) Plant Physiol. 87, 250–254.

Thomas, P. S. (1980) Proc. Natl. Acad. Sci. 77, 5201.

Velten, J., Velten, L., Hain, R. and Schell, J. (1984) EMBO J.3, 2723–2730 .

Walling, L.; Drews, G. N. and Goldberg, R. (1986) Proc. Natl. Acad. Sci. 83, 2123–2127.

Yang, F., Luna, V. G., McAnelly, R. D., Noberhaus, K. H., Cupples, R. L., Bowman, B. H. (1985) Nucl. Acids Res. 13, 8007–8017.

Youle, R. and Huang, A. H. C. (1981) American J. Bot. 68, 44–48.

TABLE 1

| 2S Albumin As % Of Total Seed Protein | |
|---|---|
| Family, species (common name) | % |
| Compositae *Helianthus annuus* (sunflower) | 62 |
| Cruciferae Brassica spp. (mustard) | 62 |
| Linaceae *Linum usitatissimum* (linseed) | 42 |
| Leguminosae | |
| *Lupinus polyphyllus* (lupin) | 38 |
| *Arachis hypogaea* (peanut) | 20 |
| Lecythidaceae *Bertholletia excelsa* (brazil nut) | 30 |
| Liliaceae Yucca spp. (yucca) | 27 |
| Euphorbiaceae *Ricinus communis* (castor bean) | 44 |

From Youle and Huang, 1981

We claim:

1. A seed-forming plant susceptible to Agrobacterium transformation; the genome of said plant comprising a recombinant DNA encoding a precursor of a modified 2S albumin, under the control of a promoter, said recombinant DNA comprising:

a nucleic acid sequence encoding a precursor of a 2S albumin from Brassica species, an Arabidopsis species, *Ricinus communis* or *Bertholletia excelsa*, wherein a second DNA sequence is inserted into or replaces in part a region of said nucleic acid sequence between (i) a third codon downstream of a codon encoding a fourth cysteine residue and (ii) a third codon upstream of a codon encoding a fifth cysteine residue of the large subunit of said 2S albumin and wherein said second DNA sequence encodes a polypeptide containing an amino acid selected from the group consisting of a lysine, a methionine, a tryptophan, a threonine, a phenylalanine, a leucine, a valine, an arginine and an isoleucine; and whereby said precursor of said modified 2S albumin is expressed and said modified 2S albumin or said precursor of said modified 2S albumin is stored in said plant.

2. The seed-forming plant of claim 1 wherein said 2S albumin is from *Aribidopsis thaliana* or *Brassica napus*.

3. The seed-forming plant of claim 1 which is an Arabidopsis or Brassica.

4. The seed-forming plant of claim 3 which is *Brassica napus*.

5. The seed-forming plant of claim 1, wherein said second DNA sequence encodes a plurality of said amino acids.

6. A seed of the plant of claim 1.

7. A seed of the plant of claim 2.

8. A seed of the plant of claim 3.

9. A seed of the plant of claim 4.

10. A seed of the plant of claim 5.

11. The seed-forming plant of claim 1, wherein second DNA sequence is located between condons which code for amino acids 31 and 57 of the large subunit of the 2S albunim of *Arabidopsis thaliana*.

12. The seed-forming plant of claim 11, wherein the 2S albumin is AT2S1.

13. A seed-forming plant susceptible to Agrobacteirum transformation; the genome of said plant comprising a recombinant DNA encoding a precursor of a modified 2S albumin, under the control of a promoter, said recombinant DNA comprising:

A nucleic acid sequence encoding a precursor of a 2S albumin from Brassica species, an Arabidopsis species, *Ricinus communis* or *Bertholletia excelsa*, wherein a second DNA sequence is inserted into or replaces in part a region of said nucleic acid sequence between (i) a sixth codon downstream of a codon encoding a fourth cysteine residue and (ii) a sixth codon upstream of a codon encoding a fifth cysteine residue of the large subunit of said 2S albumin and wherein said second DNA sequence encodes a polypeptide containing an amino acid selected from the group consisting of a lysine, a methionine, a tryptophan, a threonine, a phenylalanine, a leucine, a valine, an arginine and an isoleucine; and whereby said precursor of said modified 2S albumin is expressed and said modified 2S albumin or said precursor of said modified 2S albumin is stored in said plant.

14. The seed-forming plant of claim 13 wherein said 2S albumin free from *Arabidopsis thaliana* or *Brassica napus*.

15. The seed-forming plant of claim 13, which is an Arabidopsis or Brassica.

16. The seed-forming plant of claim 15, which is *Brassica napus*.

17. The seed-forming plant of claim 13, wherein said second DNA sequence encodes a plurality of said amino acids.

18. A seed of the plant of claim 13.

19. A seed-forming plant susceptible for Agrobacterium transformation; the genome of said plant comprising a recombinant DNA encoding a precursor of a modified 2S albumin, under the control of a promoter, said recombinant DNA comprising:

a nucleic acid sequence encoding a precursor of a 2S albumin from the genera Brassica and Arabidopsis, wherein a second DNA sequence is inserted into or replaces in part a region of said nucleic acid sequence between (i) a third codon downstream of a codon encoding a fourth cysteine residue and (ii) a third codon upstream of a codon encoding a fifth cysteine residue of the large subunit of said 2S albumin and wherein said second DNA sequence encodes a polypeptide containing an amino acid selected from the group consisting of a lysine, a methionine, a tryptophan, a threonine, a phenylalanine, a leucine, a valine, an arginine and an isoleucine; and whereby said precursor of said modified 2S albumin is expressed and said modified 2S albumin or said precursor of said modified 2S albumin is stored in said plant.

* * * * *